United States Patent [19]

Patel

[11] Patent Number: 5,612,474
[45] Date of Patent: Mar. 18, 1997

US005612474A

[54] ACID LABILE IMMUNOCONJUGATE INTERMEDIATES

[75] Inventor: Vinod F. Patel, Carmel, Ind.

[73] Assignee: Eli Lilly and Company, Indianapolis, Ind.

[21] Appl. No.: 269,493

[22] Filed: Jun. 30, 1994

[51] Int. Cl.$^6$ .................... C07H 19/173; C07H 19/16; C07H 17/08

[52] U.S. Cl. .......................... 536/27.14; 536/7.1

[58] Field of Search ................ 536/25.5, 27.1, 536/25.3, 27.14, 7.1

[56] References Cited

U.S. PATENT DOCUMENTS

| | | | |
|---|---|---|---|
| 3,462,414 | 8/1969 | Wechter et al. | 536/25.5 |
| 4,376,765 | 3/1983 | Trouet et al. | 424/127 |
| 4,569,789 | 2/1986 | Blattler et al. | 260/112 R |
| 5,084,560 | 1/1992 | Hellstrom et al. | 530/390 |

FOREIGN PATENT DOCUMENTS

0424819A1  5/1991  European Pat. Off. .

*Primary Examiner*—Gary L. Kunz
*Attorney, Agent, or Firm*—Donna K. Blalock; Paul J. Gaylo; David E. Boone

[57] ABSTRACT

Trityl derivatives useful as "linkers" for preparation of imunoconjugates comprising drugs end antibodies are provided. Immunoconjugates and processes for their preparation and use are also provided. This invention also provides for prodrugs comprising a substituted trityl group conjugated with a drug of choice as well as methods of using the imunoconjugates and prodrugs of this invention.

8 Claims, No Drawings

ACID LABILE IMMUNOCONJUGATE INTERMEDIATES

FIELD OF THE INVENTION

The present invention provides acid labile immunoconjugates comprising an antibody or fragment thereof, a chemotherapeutic agent and a "linker" for joining the drug to the antibody and thus belongs to the fields of organic chemistry, pharmaceutical chemistry and immunology.

BACKGROUND OF THE INVENTION

The science of pharmaceutical chemistry has progressively provided more and more specific and potent drugs for the treatment and prevention of illnesses. However, until quite recently, there has been no means to direct a drug to the specific part of the body where it is needed. Thus, although it is often possible to treat a patient with a drug which has the specific effect which is needed, and no other effect on the body, it is still necessary to administer a whole-body dose. On the other hand, if it were possible to direct a drug to the organ, tissue or even cell in need of the treatment, it would often be possible to administer an extremely small total dose, since the drug would concentrate itself where it is needed. The advantage in safety to the patient and economy of the drug is obvious.

The present invention provides immunoconjugates which utilize derivatized trityl groups to generate a genus of immunoconjugates which provide for release of therapeutic agents at various degrees of acidity or alkalinity. The flexibility thus afforded by the ability to preselect the pH range at which the therapeutic agent will be released allows the clinician to select an appropriate immunoconjugate based on the known physiological differences between tissues in need of delivery of a therapeutic agent, the known antigenic specificity of literally hundreds of monoclonal antibodies which are now available, and various therapeutic agents amenable to use in the immunoconjugates of the present invention.

The present invention provides immunoconjugates useful in numerous therapeutic areas, but is especially well suited to deliver oncolytics. The acidity (pH) of tumor tissues appears to be lower than that of normal tissues. Studies conducted more than half a century ago showed that malignant tumors metabolize carbohydrates mainly by anaerobic glycolysis, even under aerobic conditions. Warburg et al., *Biochem. F.*, 152:309 (1924). The oxidation of glucose stops at the stage of glucose oxidation to pyruvic acid, followed by reduction to lactic acid. Boxer and Devlin, *Science*, 134:1495 (1961). Most of this lactic acid is either removed or buffered by surrounding extracellular fluid, but some of it accumulates extracellularly. This results in a lower pH within the tumor than in normal tissues. Elevation of the blood-sugar by intravenous infusion of glucose should accelerate anaerobic metabolism resulting in even more lactic acid in the tumor, and this should further increase the pH difference between tumors and normal tissues.

Following Warburg's studies, there have been several reports of lower pH in tumors of both experimental animals [See, e.g., Voegtlin, et al., *National Institutes of Health Bulletin*, 164:1 (1935); Hahler and Robertson, *Journal of the National Cancer Institute*, 3:495 (1943)] and human patients. Naeslund, *Acta Soc. Med. Upsal.*, 60:150 (1955); Pampus, *Acta Neurochir.*, 11:305 (1963).

Meyer et al., in *Cancer Research*, 8:513 (1948), reported that the pH of malignant human tumors is lower than in normal tissues. In twelve out of fourteen cases, where both normal and neoplastic tissues from the same patients could be studied in vivo, there was a difference in pH which averaged 0.49 and ranged from 0.17 to 1.15.

Ashby, [*The Lancet*, Aug. 6, p. 312 (1966)], found that the mean pH of malignant tumors from nine patients was 6.8 (ranging between 6.6 and 6.9). Raising of the blood sugar by intravenous infusion of dextrose further decreased the tumor pH to a mean of 6.5 (range 6.3–6.8).

Van Den Berg, et al., *European Journal of Cancer and Clinical Oncology*, 18:457 (1982), showed that the pH of twenty-two human mammary carcinomas was 7.29 ($\pm 0.05$, SEM), as compared to 7.63 ($\pm 0.03$, SEM) in human subcutis, and observed similar differences in rat tumors. The differences between pH in tumors and normal tissues were highly statistically significant, although they were lower than those reported in the studies discussed above.

Thistlethwaite, et al., *Int. J. Radiation Oncology Biol. Phys.* 11:1647 (1985), showed, likewise, that the pH of human tumors as measured by readings on fourteen tumors was below the physiological level with an average of $6.81 \pm 0.09$ (SEM). They speculated that the reported therapeutic effectiveness of hyperthermia depends on the lower extracellular pH of tumors as compared to normal tissues.

Trouet et al., U.S. Pat. No. 4,376,765, describe drug compounds composed of a protein macromolecule (carrier) linked via a peptide chain ("spacer arm") to an amino function of a drug. The carrier facilitates endocytic take-up by target cells so that the spacer arm may be cleaved within the cell. Recently, attention has been directed to developing antibody drug conjugates which release a drug within a tumor cell once the conjugate has crossed the cell membrane and encountered acidic pH (3.5–5.5) within the cell. U.S. Pat. No. 4,569,789 issued to Blattler, et al., describes chemical formation of conjugates using crosslinking structures which can link amino-group substances such as chemotherapeutic drugs to the sulfhydryl portion of a compound such as an antibody reactive with tumor cell surface antigens capable of crossing the tumor cell membrane. One limitation of such a method of forming conjugates is that the antibody must contain a sulfhydryl group. This reduces the number of possible drug-antibody conjugates which may be formed using such procedures.

U.S. Pat. No. 5,084,560 describes peptide-based "linkers" which release at lower pH values and describes studies wherein the lower pH values of tumors were measured.

European Patent Application 0 424 819 A1 describes the preparation of trityl derivatives and describes their use as protecting agents for the reversible modification of a variety of natural products, biopolymers and the like.

SUMMARY OF THE INVENTION

The present invention provides a physiologically acceptable drug conjugate of Formula I:

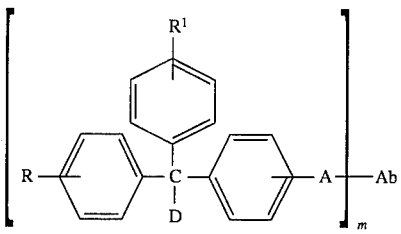

wherein:
R and $R^1$ are independently selected from the group consisting of:
—$NO_2$, —CHO, —COOH, —$CO_2X$, —$PO_2X$, —$CBr_3$, —$CCl_3$, —$CF_3$, —$CI_3$, —COX, —CN, —$CONH_2$, —OC(O)OX, —OC(O)NHX, —OC(O)$NX_2$, —$CH_2Cl$, —$CH_2X$, —$CH_3$, —$CHX_2$, —$CX_3$, —F, —Cl, —Br, —I, —H, —$NH_2$, —SH, —OPOX, —OH, —OX, —$OCO_2X$, —SX, —$SONH_2$, —$S(O)_nX$, —$SO_2NH_2$, —$SO_2NHX$, —SONHX, —NHX, and —$NX_2$,
where X is $C_1$–$C_{12}$ alkyl or aryl, and
n is 0–3;

m is 1–10;
Ab is an antibody, an antibody fragment, or immunologically functional equivalent thereof;
D is a drug having a reactively available nucleophilic group;
A is

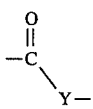

wherein y is a bond, $C_1$–$C_{12}$ alkyl, $C_2$–$C_{12}$ alkenyl, $C_2$–$C_{12}$ alkynyl, $C_1$–$C_{12}$ alkoxy, $C_1$–$C_{12}$ alkylthio, $C_1$–$C_{12}$ alkylamino, aryl, arylamino, aralkylamino, arylthio, aryloxy, aralkyl, aralkylamino, aralkalkylamino, aralkylthio, aralkoxy, or a peptide having from 0–6 amino acids.
or a salt thereof.

The present invention also provides drug-linker intermediates of Formula II:

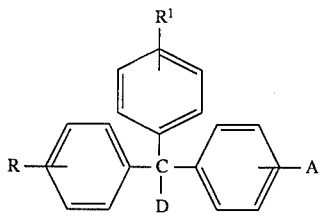

wherein:
R and $R^1$ are independently selected from the group consisting of:
—$NO_2$, —CHO, —COOH, —$CO_2X$, —$PO_2X$, —$CBr_3$, —$CCl_3$, —$CF_3$, —$CI_3$, —COX, —CN, —$CONH_2$, —OC(O)OX, —OC(O)NHX, —OC(O)$NX_2$, —$CH_2Cl$, —$CH_2X$, —$CH_3$, —$CHX_2$, —$CX_3$, —F, —Cl, —Br, —I, —H, —$NH_2$, —SH, —OPOX, —OH, —OX, —$OCO_2X$, —SX, —$SONH_2$, —$S(O)_nX$, —$SO_2NH_2$, —$SO_2NHX$, —SONHX, —NHX, and —$NX_2$, where X is $C_1$–$C_{12}$ alkyl or aryl, and
n is 0–3;

D is a drug having a reactively available nucleophilic group;
A is

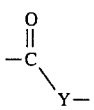

wherein y is a bond, $C_1$–$C_{12}$ alkyl, $C_2$–$C_{12}$ alkenyl, $C_2$–$C_{12}$ alkynyl, $C_1$–$C_{12}$ alkoxy, $C_1$–$C_{12}$ alkylthio, $C_1$–$C_{12}$ alkylamino, aryl, arylamino, aralkylamino, arylthio, aryloxy, aralkyl, aralkylamino, aralkalkylamino, aralkylthio, aralkoxy, or a peptide having from 0–6 amino acids.
or a salt, solvate, or prodrug thereof.

In another embodiment this invention provides prodrugs of Formula III

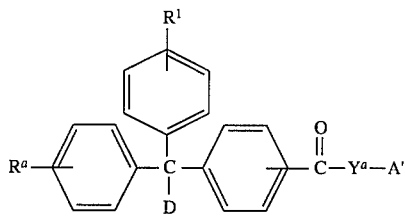

wherein:
$R^a$ and $R^1$ are independently selected from the group consisting of
—$NO_2$, —CHO, —COOH, —$CO_2X$, —$PO_2X$, —$CBr_3$, —$CCl_3$, —$CF_3$, —$CI_3$, —COX, —CN, —$CONH_2$, —OC(O)OX, —OC(O)NHX, —OC(O)$NX_2$, —$CH_2Cl$, —$CH_2X$, —$CH_3$, —$CHX_2$, —$CX_3$, —F, —Cl, —Br, —I, —H, —$NH_2$, —SH, —OPOX, —OH, —OX, —$OCO_2X$, —SX, —$SONH_2$, —$S(O)_nX$, —$SO_2NH_2$, —$SO_2NHX$, —SONHX, —NHX, and —$NX_2$,
where x is $C_1$–$C_{12}$ alkyl or aryl, and
n is 0–3;
$Y^a$ is —NH—, —S—, —O—, or —$CH_2$—;
A' is $C_1$–$C_{12}$ alkyl, aryl, heterocyclic, unsaturated heterocyclic, heterocyclic-($C_1$–$C_{12}$ alkylidenyl)-, unsaturated heterocyclic-($C_1$–$C_{12}$ alkylidenyl)-, aryl-($C_1$–$C_{12}$ alkylidenyl)-, $C_2$–$C_{12}$ alkenyl, or $C_2$–$C_{12}$ alkynyl, or a peptide of 1 to 6 amino acids;
or a pharmaceutically acceptable salt or solvate thereof.

The invention also provides pharmaceutical compositions comprising a conjugate of the invention and a parenterally-administrable medium, and treatment methods comprising administering a conjugate of the invention to a patient in need of treatment with the drug.

This invention also provides pharmaceutical compositions comprising a prodrug as described above, or a salt or solvate of said prodrug, in combination with one or more pharmaceutically acceptable carriers, diluents or excipients.

DETAILED DESCRIPTION OF THE INVENTION

Throughout the present document, all temperatures are in degrees Celsius. All expressions of percentage, concentration and the like are in weight units, unless otherwise stated. All references to concentrations and dosages of drug conjugates are in terms of the amount or concentration of the drug contained in the conjugate. The antibody, linker and drug components of the immunoconjugates of the present invention will be discussed individually prior to discussion of the assembly of the immunoconjugates.

The terms and abbreviations used in the instant examples have their normal meanings unless otherwise designated. For example "°C." refers to degrees Celsius; "N" refers to normal or normality; "mmol" refers to millimole or millimoles; "g" refers to gram or grams; "ml" means milliliter or milliliters; "M" refers to molar or molarity; "MS" refers to mass spectrometry; "IR" refers to infrared spectroscopy; and "NMR" refers to nuclear magnetic resonance spectroscopy.

As used herein, the term "$C_1$–$C_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl.

"Halo" represents chloro, fluoro, bromo or iodo.

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like.

The term "$C_2$–$C_{12}$ alkynyl" refers to a straight or branched, monovalent, unsaturated aliphatic chain having from two to twelve carbon atoms and containing at least one triple bond. Typical $C_2$–$C_{12}$ alkynyl groups include ethynyl, 1-propynyl, 1-butynyl, 1-hexynyl, 2-propynyl, 2-pentynyl, and the like.

The term "$C_2$–$C_{12}$ alkenyl" as used herein represents a straight or branched, monovalent, unsaturated aliphatic chain having from two to twelve carbon atoms. Typical $C_2$–$C_{12}$ alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 1-butenyl, 2-pentenyl, and the like.

"$C_1$–$C_6$ alkylidenyl" represents a straight or branched divalent alkyl chain having from one to four carbon atoms. Typical $C_1$–$C_6$ alkylidenyl groups include methylene, ethylene, propylene, 2-methylpropylene, butylene and the like.

"$C_1$–$C_{12}$ alkylthio" represents a straight or branched alkyl chain having from one to four carbon atoms attached to a sulfur atom. Typical $C_1$–$C_{12}$ alkylthio groups include methylthio, ethylthio, propylthio, isopropylthio, butylthio and the like. The term "$C_1$–$C_{12}$ alkylthio" includes within its definition the term "$C_1$–$C_6$ alkylthio".

"$C_1$–$C_{12}$ alkylamino" represents a straight or branched alkylamino chain having from one to twelve carbon atoms attached to an amino group. Typical $C_1$–$C_4$ alkylamino groups include methylamino, ethylamino, propylamino, isopropylamino, butylamino, sec-butylamino and the like.

"Di($C_1$–$C_{12}$)alkylamino" represents a straight or branched dialkylamino chain having two alkyl chains, each having independently from one to twelve carbon atoms attached to a common amino group. Typical di($C_1$–$C_{12}$)alkylamino groups include dimethylamino, ethylmethylamino, methylisopropylamino, t-butylisopropylamino, di-t-butylamino and the like.

"$C_2$–$C_{12}$ alkanoyl" represents a straight or branched alkyl chain having from one to eleven carbon atoms attached to a carbonyl moiety. Typical $C_2$–$C_{12}$ alkanoyl groups include acetyl, propanoyl, isopropanoyl, butanoyl, t-butanoyl, pentanoyl, hexanoyl, 3-methylpentanoyl and the like.

"Aryl" represents a phenyl or naphthyl ring.

The term "leaving group" as used herein refers to a group of atoms that is displaced from a carbon atom by the attack of a nucleophile in a nucleophilic substitution reaction. The term "leaving group" as used in this document encompasses, but is not limited to, activating groups.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and preferably may be, for example, succinimidoxy, phthalimidoxy, benzotriazolyloxy or —O—CO—($C_4$-$C_7$ alkyl).

The term "heterocycle" represents an unsubstituted or substituted stable 5- to 7-membered monocyclic or 7- to 10-membered bicyclic heterocyclic ring which is saturated and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure.

The term "unsaturated heterocycle" represents an unsubstituted or substituted stable 5- to 7-membered monocyclic or 7- to 10-membered bicyclic heterocyclic ring which has one or more double bonds and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The unsaturated heterocyclic ring may be attached at any heteroatom or carbon atom which affords a stable structure.

Examples of such heterocycles and unsaturated heterocycles include piperidinyl, piperazinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinylsulfoxide, thiamorpholinylsulfone, oxadiazolyl, triazolyl, tetrahydroquinolinyl, and tetrahydroisoquinolinyl.

The Antibody

It will be understood that the function of the present drug conjugates is determined by the biological efficacy of the drug and the antigenic selectivity of the antibody. An antibody is chosen which will recognize an antigen associated with a cell to which the particular drug is beneficially delivered. For example, if the drug is an anti-neoplastic, then an antibody which recognizes an antigen associated with tumor cells would be chosen. A further application of anti-proliferative agents, such as the anti-neoplastic is in the treatment of cardiovascular disease. It is now well established that restinosis frequently follows angioplasty. The site-specific delivery of anti-proliferatives to areas where atherosclerotic plaque was removed by angioplasty would be useful in retarding or preventing re-occlusion. If the drug is an antibacterial, for example a cephalosporin, an antibody would be chosen which recognizes a bacterial antigen.

Depending on the characteristics of the drug to be used, it may be preferred in a given case to choose an antibody or antigen recognizing fragment thereof which is internalized by the cell, or it may be preferred to use an antibody or antigen binding fragment thereof which remains on the cell surface by recognizing a surface antigen.

The source of the antibody is not critical to the present invention. It may be chosen from any class or subclass of immunoglobulin, including IgG, IgA, IgM, IgE, IgD, and the like. Similarly, the species of origin is not critical so long as the antibody targets a cell where the effect of the drug is useful.

In the present state of the art, monoclonal antibodies are frequently used in drug conjugates, and use of them is preferred in the present invention. However, polyclonal antibodies are not excluded. Genetically engineered antibodies which retain the epitope specificity of monoclonal antibodies are now known in the art and provide a less immunogenic molecule. Such genetically engineered antibodies are also embraced by the present invention. Chimeric antibodies are described in U.S. Pat. No. 4,816,567, which issued Mar. 28, 1989. The entire contents of U.S. Pat. No. 4,816,567 (Cablily) are herein incorporated by reference. A further approach to production of genetically engineered antibodies is provided in U.S. Pat. No. 4,816,397, which also issued Mar. 28, 1989. The entire contents of U.S. Pat. No. 4,816,397 (Boss) are herein incorporated by reference.

The approach of U.S. Pat. No. 4,816,397 has been further refined as taught in European Patent Publication No. 0 239 400, which published Sep. 30, 1987. The teachings of European Patent Publication No. 0 239 400 (Winter) are the preferred format for the genetic engineering of monoclonal antibodies which are used as components of the immunoconjugates of the invention. The Winter technology involves the replacement of one or more complementary determining regions ("CDR"s) of a human antibody with the CDRs of a murine monoclonal antibody thereby converting the specificity of the human antibody to the specificity of the murine antibody which was the source of the CDR regions. The CDR technology affords a molecule containing minimal murine sequences and, thus, is less immunogenic.

Single chain antibody technology is yet another variety of genetic engineered antibody which is now well known in the art. See, R. E. Bird, et al., *Science*, 242:423–426 (1988). The single chain antibody technology involves joining the binding regions of heavy and light chains with a polypeptide sequence to generate a single polypeptide having the binding specificity of the antibody from which it was derived.

The aforementioned genetic engineering approaches provide the skilled artisan with numerous means to generate molecules which retain the binding characteristics of the parental antibody while affording a less immunogenic format. Thus, genetically engineered antibodies may be obtained and used in the present invention.

The origin and nature of the antibody is not otherwise critical, so long as it targets the cell to be treated and is not, in itself, toxic to the patient. Those of ordinary skill can readily prepare conjugates with a candidate antibody and evaluate them. Some discussion of the method of evaluating antibodies and conjugates will be provided for convenience. First, the antibody should be produced by a cell-line which is sufficiently stable to allow preparation of reasonable quantities of antibody. The antibody itself should be amenable to purification and in particular should be sufficiently water-soluble to allow chemical manipulations at reasonable concentration.

Conjugates prepared with the candidate antibody are first evaluated for antigen-binding capacity. Skilled artisans appreciate the ease with which any diminution in antigen binding activity can be determined. Competitive radio immunoassays (RIAs) and flow cytometry are convenient means for determining whether a conjugate has reduced binding capacity relative to the pristine antibody. A modest reduction from the binding capacity of the free antibody is expected and acceptable.

The conjugate is then tested to determine its in vitro potency, such as cytotoxicity in the case of anticancer drugs, against antigen positive cells. An effective conjugate can have potency somewhat less than the free drug in the in vitro assay, but still be more desirable because of its ability to bring a higher concentration of drug to the target site in vivo.

A conjugate which is accepted in the first two tests is then evaluated in a nude mouse human tumor xenograft model, as taught by Johnson and Laguzza, *Cancer Research*, 47:3118–3122 (1987). The candidate conjugate should be tested in nude mice against the free drug, a mixture of free drug and free antibody, and a conjugate with a non-targeting immunoglobulin, and should exhibit improved potency and/or safety. Dose ranging studies should be carried out in the xenograft model.

Conjugates which are potent in the xenograft model are submitted to tests in animals which are known to express the antigen of interest in a pattern similar to that seen in humans. If the conjugate produces a significant degree of binding to the antigen in such test, and if it is reasonably free of toxicity at doses predicted by the xenograft model to be therapeutic, the candidate conjugate can be considered to have therapeutic potential.

It will be understood that properly chosen fragments of antibodies have the same effect as the intact antibody. Skilled artisans realize the utility of the proteolytic enzymes papain and pepsin for cleaving immunoglobulins into fragments which are bivalent or monovalent respectively. Thus, in the practice of this invention, fragments of antibodies, particularly $F(ab')_2$ fragments, which recognize an antigen associated with the cell to be treated, may be just as useful as are intact antibodies. Fab fragments are also useful.

One additional assay which may be employed to screen monoclonal antibodies for their potential as highly cytotoxic immunotoxins is described in U.S. Pat. No. 5,045,451, issued Sep. 3, 1991, which is hereby incorporated by reference. These assays predict the potency of a given monoclonal antibody to make an effective immunotoxin and is, therefore, useful in screening potential monoclonal antibodies for use in the conjugates of the present invention.

Formula I indicates that from 1 to 10 drug-linker moieties are attached to each molecule of antibody. Of course, the number of such moieties per antibody molecule is an average number because a given batch of conjugate will necessarily contain molecules having a range of ratios (Boltzmann distribution) of drug-linker to antibody. The most efficient use of the expensive antibody is obtained, of course, when a number of molecules of drug are attached to each antibody molecule. However, the attachment of an excessive number of molecules of drug-linker moiety usually has an adverse effect on the antibody's ability to recognize and bind to its antigen and may also cause aggregation and loss of solubility, so a compromise value for m must be found. In general, the preferred average value for m is from 3–8. Conjugation ratios are easily determined by measuring the absorbance of the immunoconjugate at wavelengths selected to detect the drug, the linker, peptide bonds, etc. and then, from the absorbance data and the extinction coefficients for the various components, deduce the average amount of drug per antibody.

A great number of antibodies are available to immunologists for use in the present invention, and further useful antibodies are frequently being disclosed in relevant journals. It is impossible, and entirely unnecessary, to give an exhaustive listing of antibodies which can be applied in the practice of this invention. Immunologists, chemists, and clinicians of ordinary skill routinely choose antibodies from sources such as the catalogue of the American Type Culture Collection, Rockville, Md., U.S.A., and Linscott's Directory of Immunological and Biological Reagents, published by Linscott's Directory, 40 Glen Drive, Mill Valley, Calif., U.S.A., 94941. The American Tissue Culture Collection is hereinafter referred to as the ATCC. References to specific hybridomas, which are available from the ATCC, will refer to the accession number assigned to the specific hybridoma by the ATCC. Thus, it is a routine matter for the artisan in the field to choose an antibody against virtually any antigen, such as tumor, bacterial, fungal, viral, parasitic, mycoplasmal, or histocompatiblity antigens, as well as pathogen surface antigens, toxins, enzymes, allergens and other types of antigens related to physiologically important cells and tissues.

The most preferred use of the present invention is in the delivery of cytotoxic drugs to cancer cells, particularly including squamous carcinoma cells, adenocarcinoma cells, small cell carcinoma cells, glyoma cells, melanoma cells, renal cell carcinoma cells, transitional cell carcinoma cells, sarcoma cells, cells of supporting tumor vasculature and cells of lymphold tumors such as leukemia and lymphomas. Appropriate antibodies for the targeting of all such cells are available, and sources can be located in Linscott. Alternatively, the necessary hybridoma for the production of such antibodies by conventional methods are obtainable through ATCC and other cell line collections.

A number of presently known antibodies are particularly interesting for use in the anticancer aspect of the present invention. Antibodies which are preferred for purposes of the present invention are available from the ATCC and include:

| Antibody | Accession Number |
|---|---|
| L/1C2 | HB9682 |
| CC83 | HB9453 |
| CC92 | HB9454 |
| CC11 | HB9455 |
| CC112 | HB9456 |
| (Maytag 12) | |
| CC30 | HB9457 |
| CC46 | HB9458 |
| CC49 | HB9459 |
| COL-1 | |
| D612 | |
| CC15 | HB9460 |

The antibody $CC_{49}$ available under accession number ATCC HB9459 is especially preferred for purposes of the present invention.

Another especially preferred antibody is COL-1, first disclosed by Schlom, et. al., *Cancer Research* 45:5769–80 (1985).

Additional sources of antibodies useful for various therapeutic purposes are the following. Anti-human lymphocyte and monocyte antibodies, useful for immune modulation and tumor therapy, are produced by ATCC cultures HB2, HB22, HB44, HB78 and HB136. An antitransferrin receptor antibody, useful for tumor therapy, is produced by ATCC culture HB84. ATCC culture HB8059 produces an antibody against colorectal carcinoma monosialoganglioside, and culture HB8136 produces an antibody against mature human T-cell surface antigen, useful for immune modulation and T-cell leukemia therapy. ATCC hybridoma HB9620 produces an anti-carcinoembryonic antigen called CEM 231.6.7. Monoclonal antibodies useful in the diagnosis and treatment of small-cell carcinoma are reviewed in R. Stein and D. Goldberg, *Chest*, 99:1466–1476 (1991). The above list of specified antibodies is to be considered illustrative only and is not designed to limit the scope of the invention in any way.

Thus, an immunologist, clinician, or one knowledgeable in the drug targeting area, with the assistance of the commonly known publications in the field and the above guiding examples and description, can readily choose an antibody for the targeting of any appropriate drug to any desired cell to be treated with that drug.

Methods of producing and purifying monoclonal antibodies are well known to any skilled immunologist. See, e.g., "Selected Methods in Cellular Immunology", (B. Mishell and S. Shiigi, eds., 1980).

The Drug

It will be understood that the essence of the present invention is the method of linking drug and antibody by means of the above-described linkers, and that neither the drug nor the antibody is a limitation of the present invention. The linkers of the present invention, accordingly, may be and are used beneficially when applied to drugs of any therapeutic or prophylactic purpose, limited only by the necessity for the drug to have a chemical functionality with which the trityl linker can be attached, and the necessity for the antibody to target a cell or tissue where the drug is beneficial. The trityl linker is reactive with any drug possessing a reactively available nucleophilic functional group such as, for example: hydroxy; amino; sulfhydryl; carboxy;

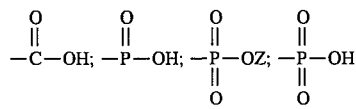

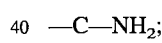

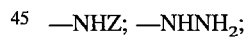

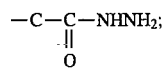

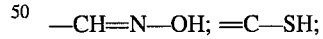

—NH—OH; —NH—OZ; —C(O)—NHNH$_2$; —C(O)—SH; and —S—(O)$_n$—OH, where n is an integer from 1–3 and where Z or Z' is $C_1$–$C_6$ alkyl or aryl;.

It will be understood that the term "trityl linker" as that term is defined and used herein includes the various substitutions set forth in Formulae I and II and further described in the section of the specification which discusses the linker.

The present linker invention may be used in connection with drugs of substantially all classes, including for example, antibacterial, antivirals, antifungals, anticancer drugs, antimycoplasmals, and the like. The drug conjugates so constructed are effective for the usual purposes for which the corresponding drugs are effective, and have superior efficacy because of the ability, inherent in the immunoconjugate, to transport the drug to the cell where it is of particular benefit, thereby increasing the effective concentration at the site.

The ability to select substitutions of the trityl group to provide release of a chosen drug at a desired pH is most beneficially applied in the construction of immunoconjugates for use in the anticancer applications due to the well-documented differences in the pH of tumor tissue relative to normal tissue. Accordingly, anticancer drugs will be discussed in more detail than the other therapeutic areas.

U.S. Pat. Nos. 5,010,176 and 4,671,958 teach BLEOMYCIN™, daunomyucin and doxorubicin and other compounds which may be subjected to drug conjugation, and the disclosures concerning drugs of those patents are herein incorporated by reference.

Chapter 1 of "The Alkaloids", Volume XXV, Academic Press, Inc., 1985 (referred to hereinafter as "The Alkaloids") reviews: antitumor alkaloids and provides an excellent overview of the alkaloids in terms of the purification, synthesis and structure activity relationships of alkaloids having antitumor activity. Taxus alkaloids such as taxol, cephalomannine, 19-hydroxybaccatin III, Baccatin V, 10-Deacetylcephalomannine, 10-Deacetyltaxol, 7-Epi-deacetyltaxol, 7-Epi-10-deacetylcephalomannine, 10-Deacetylbaccatin III, Taxol 2', 7-diacetate and 10-Deacetyltaxol 2', 7-diacetate are discussed at pages 6 to 18. "The Alkaloids" also provides detailed discussions of the Sesbanin alkaloids (pages 18–20); Pyrrolizidine alkaloids (pages 21–37); Acronycine and related compounds (pages 38–47); Ementine and related alkaloids (pages 47–56); Cephalotaxus alkaloids (pages 57–67); Colchicine (pages 67 and 68); Camptothecine and its derivatives and analogs (pages 73–88); Ellipticine and its derivatives (pages 89–141); Maytansinoids (pages 142–155); Phenanthroindozoline and Phenanthroquinolizidine alkaloids (pages 156–162); Bisisoquinoline alkaloids (pages 163–170); Benzo[c]phenanthridine alkaloids (pages 178–186); Protoberberino alkaloids (pages 188–197) and Amaryllidaceae alkaloids (pages 198–211).

"Anticancer Agents Based On Natural Products Models" (J. M. Casady and J. D. Douras, eds., Academic Press, 1980) reviews: Anthracyclines (page 142); Trichothecanes (pages 43–73); Nucleosides (Pages 73–130); Mitomycin (pages 131–147); Bleomycins (pages 148–166); Streptozocins (pages 167–200); Terpenoids (pages 200–270); Dimeric Catharanthus alkaloids (pages 271–318); Podophyllotoxins (pages 319–352); Magtansinoids (pages 353–391) and Camptothecins (pages 417–436).

Numerous scientific publications and books provide exhaustive listings of medicinal agents of use in the myriad therapeutic areas in which the immunoconjugates of the present invention find utility. For example, "USAN and the USP Dictionary of Drug Names" (United States Pharmacopeia Convention, Inc., 12601 Twinbrook Parkway, Rockville, Md. 20852) provides structures, names and therapeutic areas for current United States Pharmacopeia and NF names for drugs. As stated, the drug is reacted through a reactively available nucleophilic functionality and thus the only limitations in the choice of drug is the presence of a nucleophilic group and the desired therapeutic activity.

The most preferred efficacy class of drugs for use in the present invention is the class of cytotoxic drugs, particularly those which are used for cancer therapy. Such drugs include, in general, alkylating agents, anti-proliferative agents, tubulin binding agents, and the like. Preferred classes of cytotoxic agents include, for example, nucleoside analogs, the anthracycline family of drugs, the vinca drugs, the mitomycins, and the like. Especially preferred drugs include difluronucleosides and daunomycin, and derivatives of daunomycin, with doxorubicin being an especially preferred daunomycin and gemcitabine and 2-Amino-2'-deoxy-2',2'-difluoroadenosine (hereinafter referred to as "ADDFA") being especially preferred difluronucleosides. It will be understood that chemical modifications may be made by the ordinarily skilled chemist to the preferred and generally described compound in order to make reactions of them more convenient.

The term "Cytotoxic Agent" as used herein refers to compounds that are useful in the treatment of neoplasms, whether benign or malignant. Such drugs include, in general, alkylating agents, antiproliferative agents, tubulin-binding agents, cytotoxins in general, and the like. Preferred classes of such compounds are the nitrogen mustard agents, anti-folates, nucleoside analogs, the vinca alkaloids, the anthracyclines, the mitomycins, the bleomycins, the cytotoxic nucleosides, the pteridine family of drugs, the podophyophyllotoxins, the sulfonylureas (as described in U.S. Pat. Nos. 5,254,582, 4,845,128, 5,116,874, 5,110,830, 5,260,338, 5,169,860, and 5,262,440, the entire contents of which are herein incorporated by reference), and low-molecular-weight toxins such as the trichothecenes and the colchicines. Particularly useful members of those classes include, for example, doxorubicin, daunorubicin, aminopterin, methotrexate, taxol, methopterin, dichloromethotrexate, mitomycin C, porfiromycin, 5-fluorouracil, 6-mercaptopurine, cytosine arabinoside, podophyllotoxin, etoposide, melphalan, vinblastine, vincristine, desacetylvinblastine hydrazide, leurosidine, vindesine, leurosine, trichothecene, desacetylcolchicine and the like.

General structural formulas of several of the preferred classes of oncolytic agents are provided below as Formulas III through XIV.

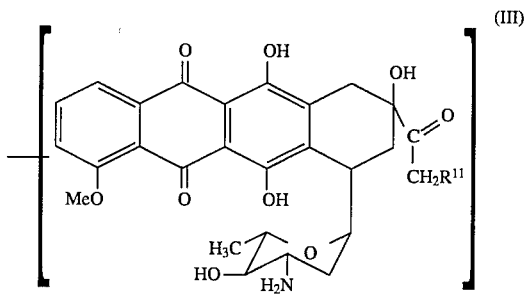

wherein $R^{11}$ is hydrogen or hydroxy;

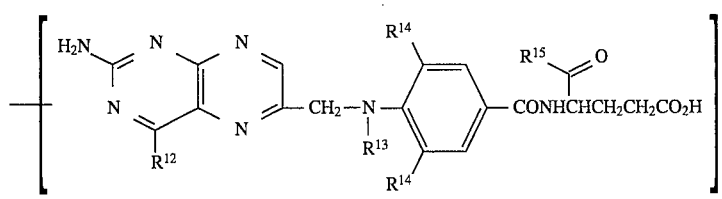 (IV)
wherein
- $R^{12}$ is amino or hydroxy;
- $R^{13}$ is hydrogen or methyl;
- $R^{14}$ is hydrogen, fluoro, chloro, bromo, iodo;
- $R^{15}$ is hydroxy or a moiety which completes a salt of the carboxylic acid;
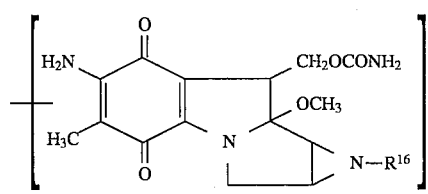 (V)
wherein $R^{16}$ is hydrogen or methyl;
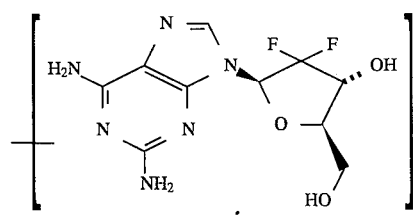 (VI)
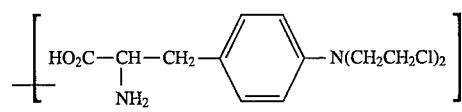 (VII)
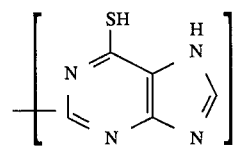 (VIII)
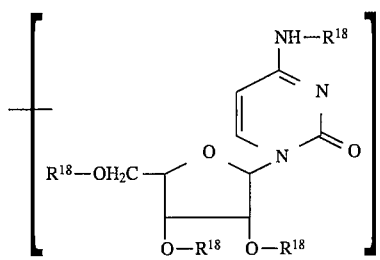 (IX)
wherein one of the $R^{18}$ moieties is a bond and the others are hydrogen;
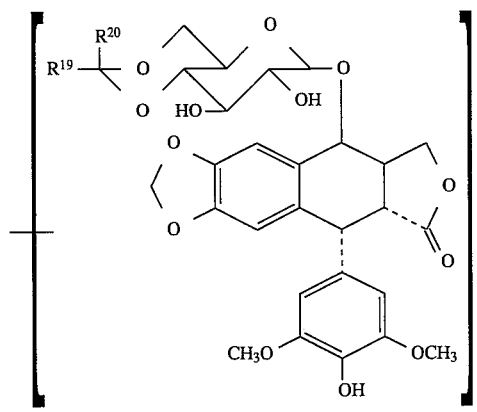 (X)
wherein
- $R^{19}$ is hydrogen or methyl;
- $R^{20}$ is methyl or thienyl;

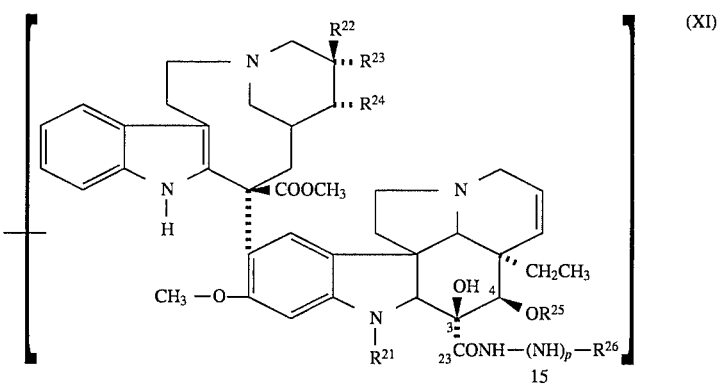
(XI)

wherein $R^{21}$ is H, $CH_3$ or CHO; when $R^{23}$ and $R^{24}$ are taken singly, $R^{24}$ is H, and one of $R^{22}$ and $R^{23}$ is ethyl and the other is H or OH; when $R^{23}$ and $R^{24}$ are taken together with the carbons to which they are attached, they form an oxirane ring in which case $R^{22}$ is ethyl; $R^{25}$ is hydrogen, $(C_1$-$C_3$ alkyl)-CO—, or chloro-substituted $(C_1$-$C_3$ alkyl)-CO—;

p is 0 or 1;

$R^{26}$ is —$(C_2$-$C_4$ alkyl)-X, or a group that requires that p is 1 and which is in turn bonded to a carbonyloxy group;

X is —O—, —S—, or —NH—;

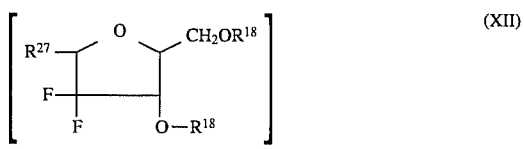
(XII)

wherein $R^{27}$ is a base of one of the formulae:

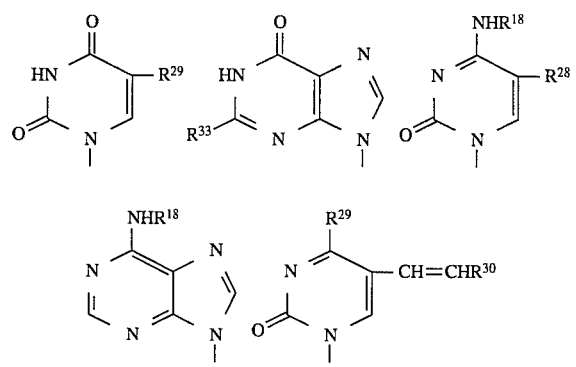

wherein $R^{28}$ is hydrogen, methyl, bromo, fluoro, chloro, or iodo;

$R^{33}$ is hydrogen, amino, $(C_1$-$C_{12}$ alkyl)amino, or di$(C_1$-$C_{12}$ alkyl)amino;

$R^{29}$ is —$OR^{18}$ or —$NHR^{18}$;

$R^{30}$ is hydrogen, bromo, chloro, or iodo;

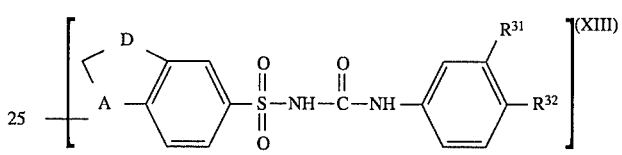
(XIII)

wherein

A is —O—, —$NCH_3$—, —$CH_2$—, —$CH_2CH_2$—, or —$CH_2O$—;

D is —$CH_2$— or —O—;

$R^{31}$ is hydrogen or halo;

$R^{32}$ is halo or trifluoromethyl;

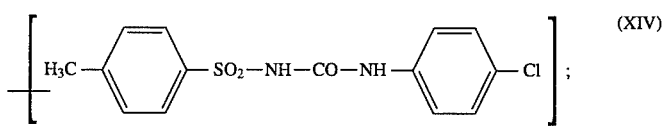
(XIV)

5-fluorouracil or desacetylcolchicine.

In the above preferred formulae, compounds of Formula III represent the anthracyclines of compounds; Formula IV represents the methotrexate group of compounds; Formula V represents the mitomycins; Formula VI represents 2-amino-2'-deoxy-2,2'-difluoroadenosine (ADDFA); Formula VII represents melphalan; Formula VIII represents 6-mercaptopurine; Formula IX represents cytosine arabinoside; Formula X represents the podophyllotoxins; Formula XI represents the vinca drugs; Formula XII represents the difluoronucleosides and Formulae XIII and XIV represent sulfonylurea compounds.

Because of the possibility of localization of a particular therapeutic, the term "drug" as used herein is not confined to those compounds which are traditionally administered systemically to a patient. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or biological response modifiers such as, for example, lymphokines, interleukin-1, interleukin-2, interleukin-6, granulocyte macrophage colony stimulating factor, granulocyte colony stimulating factor, or other growth factors.

It will also be understood that preferred conjugates are prepared from the preferred drugs. In general, it will be necessary to operate the reaction at a comparatively low concentration because the solubility of antibodies is relatively low. For example, the concentration of the antibody is usually in the range of about 5–25 mg per ml of aqueous medium.

As described above, from 1 to about 9 moles of linker and drug are attached to each mole of antibody. In order to obtain that conjugation ratio, it is usually necessary to use an excess quantity of linker intermediate.

In general, from about 4 to about 12 moles of linker intermediate per mole of antibody are used in the process. A molar input ratio (moles of linker per moles of antibody) of about 8 is especially preferred.

The reaction is allowed to proceed from a few minutes to a few hours, at temperatures in the range from about 0 to about 37 degrees Celsius. Obviously, elevated temperatures may be injurious to the antibody and it is more advisable to operate at low temperatures, particularly since the reaction is inherently rapid.

When the derivatized antibody, having the linker groups in place, has been prepared, the reaction mixture can be chromatographed by conventional procedures, as shown in the examples below, to separate the derivatized antibody from unreacted linker intermediate.

The Linker

In another embodiment the present invention provides drug-linker intermediates of Formula II:

The present invention also provides drug-linker intermediates of Formula II:

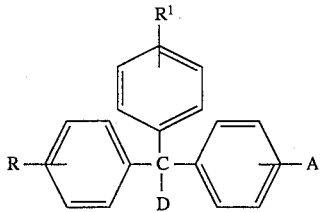

wherein:

R and $R^1$ are independently selected from the group consisting of:
—$NO_2$, —CHO, —COOH, —$CO_2X$, —$PO_2X$, —$CBr_3$, —$CCl_3$, —$CF_3$, —$CI_3$, —COX, —CN, —$CONH_2$, —OC(O)OX, —OC(O)NHX, —OC(O)$NX_2$, —$CH_2Cl$, —$CH_2X$, —$CH_3$, —$CHX_2$, —$CX_3$, —F, —Cl, —Br, —I, —H, —$NH_2$, —SH, —OPOX, —OH, —OX, —$OCO_2X$, —SX, —$SONH_2$, —$S(O)_nX$, —$SO_2NH_2$, —$SO_2NHX$, —SONHX, —NHX, and —$NX_2$,
where X is $C_1$–$C_{12}$ alkyl or aryl, and
n is 0–3;

D is a drug having a reactively available nucleophilic group;

A is

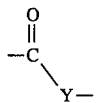

wherein y is a bond, $C_1$–$C_{12}$ alkyl, $C_2$–$C_{12}$ alkenyl, $C_2$–$C_{12}$ alkynyl, $C_1$–$C_{12}$ alkoxy, $C_1$–$C_{12}$ alkylthio, $C_1$–$C_{12}$ alkylamino, aryl, arylamino, aralkylamino, arylthio, aryloxy, aralkyl, aralkylamino, aralkalkylamino, aralkylthio, aralkoxy,or a peptide having from 0–6 amino acids.

or a salt, solvate, or prodrug thereof.

European Patent Application 0 424 819 teaches the synthesis of trityl derivatives. Minor modifications will be made to the trityl derivatives of EPA 0 424 819 to facilitate linkage of the trityl derivative to appropriate antibodies. Some of the trityl derivatives of the present invention may be prepared essentially as described in U.S. Pat. No. 3,440,190, issued Apr. 22, 1969, the entire contents of which is herein incorporated by reference.

The preferred means for attaching trityl derivatives to antibodies is by means of an amide bond formed between an active ester of the trityl derivative and a lysine molecule of the antibody. Numerous other functionalities may also be introduced into the trityl derivatives of the present invention for linkage to appropriate reactively available groups on the corresponding antibody. For example, trityl derivatives containing a sulfhydryl group are useful for attaching the thus functionalized trityl derivative by means of disulfide bonding to cysteine or methionine residues of the antibody. Hydrazide groups may also be attached to the trityl derivatives of the present invention for purposes of linkage to reactively available carbonyl functions of the antibody.

The reduction of carbohydrates to generate the corresponding aldehyde or ketone is well known in the art. Periodate or enzyme-mediated reduction of the carbohydrates on the antibody to generate the desired carbonyl which is then reacted with the hydrazide substitution of the trityl derivative is taught in U.S. Pat. No. 5,144,012, issued Sep. 1, 1992 to D. A. Johnson, et al., which is herein incorporated by reference. Thus, numerous options are available for attachment of the trityl derivatives to the antibody.

Attachment of linkers and other molecules to the lysine of an antibody or other protein is taught in A. H. Blair and T. I. Ghose, *Journal of Immunological Methods*, Volume 59, pp. 129–143, 1983. Additional sources of information on attachment of organic molecules to proteins is found in "Chemistry of Protein and Cross Linking", CRC Press, (S. S. Wong, ed. 1991) and other references.

The reaction between the drug of choice and the trityl linker of the present invention affords a great deal of flexibility in selection of an appropriate drug. The only requirements are that the drug be of an appropriate therapeutic class for the specific targeting purpose of the immunoconjugate and that it contain a reactively available nucleophilic group which can undergo an alkylation. Most preferred drugs of choice for use in the present invention are anti-cancer drugs.

Drug-Linker Moieties as Prodrugs

The preferred use of the drug-linker aspect of the present invention is for use in preparing the antibody-drug-linker acid labile immunoconjugates of the present invention. The drug-linker moieties by themselves have shown substantial promise as prodrugs and allow the administration of a drug which otherwise showed too much cardiotoxicity for use in oncolytic therapy. The trityl group alters the pharmacology of the 2,6-diamino-difluoro nucleoside described below and provides a therapeutic benefit without the attendant toxicity observed with the "free-drug".

The ability to readily acylate nucleophiles, e.g. alcohols, amines, mercaptans, and the like, with the drug-linker active esters allows rapid access to numerous, different prodrugs which may possess varying chemical, physical, or pharmacological properties which may provide a therapeutic benefit. Such properties may include enhanced stability, increased bioavailability, diminished metabolism, reduced toxicity, cellular or tissue compartmentalization, enhanced permeability across a natural barrier such as the blood-brain barrier, amenability to different formulations, ease of synthesis, and the like.

Thus, the drug-linker moiety of the present invention alone possesses an unexpected utility as a prodrug. The present invention, therefore, encompasses these novel prodrugs employing a trityl moiety as described supra.

Synthesis of the Conjugates

When a modified drug is made, and is reacted with the antibody as the final step in preparing the conjugate, the above observations concerning the precautions pertinent to reactions with antibodies are entirely applicable. The same principles govern the choice of the ratio between the amount of antibody and the amount of derivatized drug. In general, the reaction conditions must be chosen with regard to the stability of the antibody, since the drug can generally be expected to tolerate any conditions which the antibody will tolerate.

When a modified antibody is made, and reaction with the drug is the final step, precautions to assure the stability of the antibody must be observed.

Accordingly, the preferred process is to make a drug-linker moiety and then to react it with the antibody as the final step. Reaction of the modified antibody with the drug-linker must be carried out at comparatively low temperatures as stated above, and in a medium which the antibody can tolerate. For example, a particularly useful reaction medium is borate buffer, especially 0.05–0.2M borate buffer at a pH of about 8.60. Small amounts of organic solvents in the reaction medium are not harmful, as discussed above, so long as the solvents do not have a tendency to damage the antibody. Dimethylformamide at a final concentration of 7.5% is an especially preferred organic solvent.

Finally, the drug conjugate is purified and isolated, customarily by chromatographic methods. It may be possible to elute a conjugate from the chromatography medium in a concentration which is appropriate for administration to patients. Customarily, however, the conjugate will be purified by chromatography, eluting with any convenient solvent, but most preferably with physiological buffered saline, and then concentrating by established means to the desired concentration for administration.

Compositions and Methods of Use

The conjugates of the present invention are useful in the treatment methods which are important parts of the present invention. Accordingly, the invention also includes pharmaceutical compositions for parenteral administration which are used in the treatment methods. Such compositions are formulated by methods commonly used in pharmaceutical chemistry. The present conjugates are acceptably soluble in physiologically acceptable fluids, such as physiological saline solutions and other aqueous solutions which can safely be administered parenterally.

Products for parenteral administration are often formulated and distributed in solid, preferably freeze-dried form, for reconstitution immediately before use. Such formulations are useful compositions of the present invention. Their preparation is well understood by pharmaceutical chemists; in general, they comprise mixtures of inorganic salts, to confer isotonicity, and dispersing agents such as lactose, to allow the dried preparation to dissolve quickly upon reconstitution. Such formulations are reconstituted for use with highly purified water to a known concentration.

The conjugates and compositions comprising the conjugates are used for treatment of patients who are in need of treatment with the drug comprised by the conjugate. The specific purpose of the treatment, and the dose range to be administered, depends on the identity of the drugs and the condition for which the patient is to be treated. Guidance as to the specific potencies of drug and their appropriate dosage ranges is to be obtained from the standard medical literature.

Synthesis of the various intermediates and the conjugates of the present invention is further explained in the examples.

EXAMPLE 1

The narrative section of the Example is complemented by the reaction scheme provided below. The Example is subdivided into sections corresponding to the same convention used in the reaction scheme to ensure understanding. For convenience, representative examples of the specific trityl linkers prepared according to the method of Example 1 are defined in Table I. The final yield of each linker is provided in Table I. The yield of each step in Example 1 is provided as the last sentence in the narrative section of the appropriate subsection.

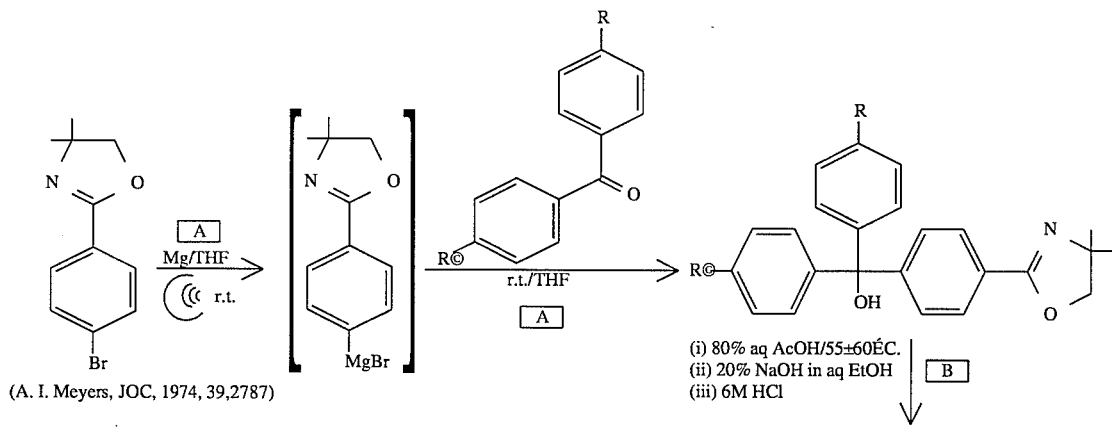

Scheme I

-continued
Scheme I

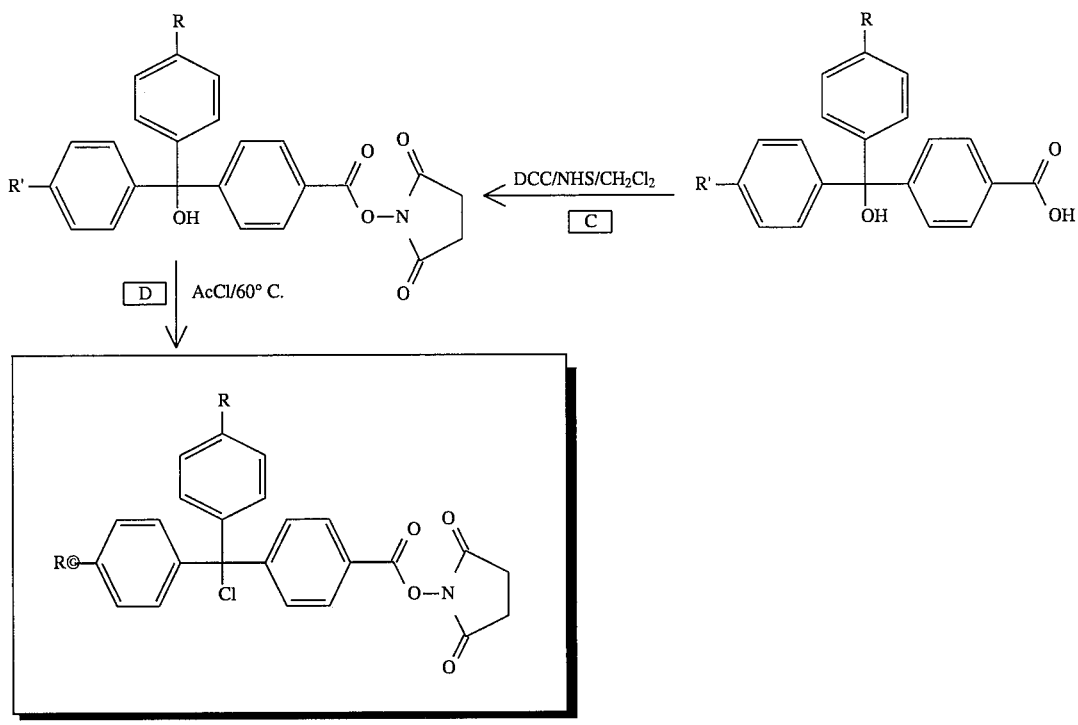

TABLE I

| | Synthesis Yields | | |
|---|---|---|---|
| Name | R | R' | Yield (%) |
| DMT | OMe | OMe | 49 |
| MMeT | OMe | Me | 30 |
| MMT | OMe | H | 36 |
| MeT | Me | H | 74 |
| T | H | H | 39 |
| m-DMT | OMe | OMe | 27 |

General Procedure A

A suspension of flame-dried magnesium turnings (1.152 g, 48 mmol) in dry tetrahydrofuran (25 ml) was sonicated for about 20 minutes, and then neat aryl bromide (10.2 g, 40 mmol) was added, followed by addition of a catalytic amount of crystalline iodine (10 mg). The mixture was further sonicated for about 30 minutes to form the Grignard reagent. A suspension of the benzophenone (44 mmol) in dry tetrahydrofuran (10 ml) was added to the Grignard solution and stirred at room temperature for about 2.5 hours under a nitrogen atmosphere.

The reaction was quenched with 5% aqueous potassium hydrgen sulphate (50 ml) and extracted with ethyl acetate (3×20 ml). The combined organics were dried over sodium sulphate and concentrated in vacuo to give a solid, which was subjected to purification by column chromatography (gradient elution 25–75% ethyl acetate in hexanes) to furnish the carbinol.

2-[3-(Bis-(4-methoxyphenyl)-hydroxymethyl)phenyl]-4,4-dimethyl-1,3-oxazoline 4,4'-Dimethoxybenzophenone (10.65 g) was reacted with the Grignard derived from 2-(3-bromophenyl)-4,4-dimethyl-1,3-oxazoline (10.20 g), essentially as described in General Procedure A, to give a white powder (11.0 g, 66%).

Tlc Rf (5% MeOH/CH$_2$Cl$_2$) 0.34 m.p. 198°–200° C.

IR (KBr) $\nu_{max}$ 3316, 2960, 1511, 1251, 1177, 1074, 1037, 825 cm$^{-1}$ $^1$H (CDCl$_3$) δ8.08 (brs, 1ArH̲),8.04–7.92 (m, 1ArH̲), 7.41–7.39 (m, 2ArH̲), 7.18 (d, J=10 Hz, 4ArH̲), 6.83 (d, J=10 Hz, 4ArH̲), 4.12 (s, CH̲$_2$), 3.78 (s, 6H, 2xOMe), 2.80 (s, OH̲), 1.40 (s, 6H, 2XMe) ppm

FDMS 417 (M+)

Analysis for C$_{26}$H$_{27}$NO$_4$: Theory: C, 74.80; H, 6.52; N, 3.36. Found: C, 74.59; H, 6.76; N, 3.45.

2-[4-(Bis(4-methoxyphenyl)-hydroxymethyl)phenyl]-4,4-dimethyl-1,3-oxazoline 4,4'-Dimethoxybenzophenone (2.66 g) was reacted with the Grignard derived from 2-(4-bromophenyl)-4,4-dimethyl-1,3-oxazoline (2.55 g), essentially as described in General Procedure A, to give the carbinol as a yellow solid (2.58 g, 62%).

Tlc Rf (10% MeOH/CH$_2$Cl$_2$) 0.32 m.p. 138°–139° C.

IR (KBr) $\nu_{max}$ 2968, 1510, 1251, 1177 cm$^{-1}$ $^1$H (CDCl$_3$) δ7.88 (d, J=8 Hz, 2ArH̲), 7.36 (d, J=8 Hz, 2Ar H̲), 7.16 (d, J=9 Hz, 4ArH̲), 6.84 (d, J=9 Hz, 4ArH̲), 4.11 (s, CH̲$_2$), 3.81 (s, 6H, 2MeO), 1.38 (s, 6H, 2Me) ppm

FDMS 417 (M+)

Analysis for C$_{26}$H$_{27}$NO$_4$: Theory: C, 74.80; H, 6.52; N, 3.36. Found: C, 74.53; H, 6.60; N, 3.19.

Racemic 2-[4-((4-methoxyphenyl)-(4-methylphenyl)hydroxymethyl)phenyl]-4,4-dimethyl-1,3-oxazoline 4,4'-Methoxymethylbenzophenone (4.89 g) was reacted with the Grignard derived from 2-(4-bromophenyl)-4,4- dimethyl-1,3-oxazoline (5.00 g), essentially as described in General Procedure A, to give the carbinol as a solid (5.73 g,72%).

Tlc Rf (50% EtOAc/Hexanes) 0.46 m.p. 64°–68° C.

IR (KBr) $v_{max}$ 2970, 1647, 1510, 1252, 1245 cm$^{-1}$ $^1$H (CDCl$_3$) δ7.98 (br d, J=6 Hz, 2ArH), 7.39 (d, J=8 Hz, 2ArH), 7.15–7.05 (m, 6ArH), 6.82 (d, J=8 Hz, 2ArH), 4.16 (br s, OCH$_2$), 3.80 (s, OMe), 2.36 (s, Me), 1.43 (s, 6H, 2 Me) ppm

FDMS 401 (M+)

Analysis for C$_{26}$H$_{27}$NO$_3$: Theory: C, 77.78; H, 6.78; N, 3.49. Found: C, 77.49; H, 7.09; N, 3.06.

Racemic 2-[4-((4-methoxyphenyl)-phenylhydroxymethyl)phenyl]-4,4-dimethyl-1,3-oxazoline 4-Methoxybenzophenone (9.34 g) was reacted with the Grignard reagent derived from 2-(4-bromophenyl)-4,4-dimethyl-1,3-oxazoline (10.20 g), essentially as described in General Procedure A, to give the carbinol as a solid (13.20 g, 85%).

Tlc Rf (25% EtOAc/Hexanes) 0.13 m.p. 62°–65° C.

IR (KBr) $v_{max}$ 2969, 1647, 1511, 1304, 1252, 1019 cm$^{-1}$ 1H (CDCl$_3$) δ7.88(d, J=8 Hz, 2ArH), 7.36 (d, J=8 Hz, 2ArH), 7.32–7.29 (m, 5ArH), 7.16 (d, J=8 Hz, 2ArH), 6.85 (d J=8 Hz, 2ArH),4.10 (s, CH$_2$), 3.80 (s, OMe), 2.80 (s, OH), 1.37 (s, 6H, 2Me) ppm

FDMS 387 (M+)

Analysis for C$_{25}$H$_{25}$NO$_3$: Theory: C, 77.49; H, 6.50; N, 3.61. Found: C, 77.73; H, 6.69; N, 3.61.

Racemic 2-[4-((4-methylphenyl)-phenyl)hydroxymethyl)phenyl]-4,4-dimethyl-1,3-oxazoline 4-Methylbenzophenone (10.53 g) was reacted with the Grignard reagent derived from 2-(4-bromophenyl)-4,4-dimethyl-1,3-oxazoline (12.40 g), essentially as described in General Procedure A, to give a white solid (18.20 g, 99%).

Tlc Rf (25% EtOAc/Hexanes) 0.33 m.p. 68°–72° C.

IR (KBr) $v_{max}$ 2971, 1647, 1274 cm$^{-1}$

U.V. (EtOH) $\lambda_{max}$ 251.5 (ε=19295), 204.5 (ε=59991) nm $^1$H (CDCl$_3$) δ7.94 (br d,J=8 Hz, 2ArH), 7.38 (d, J=8 Hz, 2ArH), 7.36–7.24 (m, 5ArH), 7.13 (s, 4ArH), 4.15 (s, OCH$_2$), 2.80 (br s, OH), 2.36 (s, Me), 1.42 (s, 6H, 2Me) ppm

FDMS 372 (M+)

Analysis for C$_{26}$H$_{27}$NO$_2$: Theory: C, 80.83; H, 6.78; N, 3.77. Found: C, 80.55; H, 7.01; N, 3.73.

2-[4-(Bis-phenyl-hydroxymethyl)phenyl]-4,4-dimethyl-1,3-oxazoline

Benzophenone (8.02 g) was reacted with the Grignard reagent derived from 2-(4-bromophenyl)-4,4-dimethyl-1,3-oxazoline (10.20 g), essentially as described in General Procedure A, to give a white solid (10.20 g, 71%).

Tlc Rf (25% EtOAc/Hexanes) 0.16 m.p. 147°–150° C.

IR (KBr) $v_{max}$ 2972, 1647, 1210 cm$^{-1}$ $^1$H (d$_6$-acetone) δ7.83 (d,J=8 Hz, 2ArH), 7.38 (d, J=8 Hz, 2ArH), 7.36–7.15 (m, 10ArH), 4.12 (s, OCH$_2$), 2.80 (s, OH), 1.30 (s, 6H, 2Me) ppm

FDMS 357 (M+)

Analysis for C$^{24}$H$_{23}$NO$_2$: Theory: C, 80.64; H, 6.49; N, 3.92. Found: C, 80.55; H, 6.58; N, 4.12.

General Procedure B

Oxazoline (22.4 mmol) was dissolved in 80% aqueous glacial acetic acid (80 ml) and then heated at reflux for about 21 hours. The clear orange solution was concentrated in vacuo at 50° C. to give an oily residue which was redissolved in 20% (w/v) sodium hydroxide in ethanol/water (1:1, 70 ml) and heated at reflux for about 3 hours. The reaction solution was concentrated, diluted with water (50 ml) and acidified with 1N aqueous hydrochloric acid to pH 3. The product was extracted with ethyl acetate (4×10 ml) and the combined organics dried over sodium sulfate and concentrated in vacuo to give the desired carboxylic acid.

3-Carboxy-4',4''-dimethoxytriphenylhydroxymethane

The corresponding oxazoline (11.00 g) was hydrolysed essentially as described in General Procedure B to give the acid as a solid (9.60 g, >99%).

IR (KBr) $v_{max}$ 3009, 2940, 1698, 1606, 1510, 1253 cm$^{-1}$ $^1$H (d$_6$-acetone) δ7.68 (d, J=8 Hz, 2ArH), 7.10 (d, J=8 Hz, 4ArH), 6.82 (d, J=8 Hz, 4ArH), 6.75 (d, J=8 Hz, 2ArH), 3.77 (s, 6 H, 2OMe) ppm FDMS for C$_{22}$H$_{20}$O$_5$ requires M 364; Found m/z 364 (100), 347 (35), 333 (65).

4-Carboxy-4',4''-dimethoxytriphenylhydroxymethane

The corresponding oxazoline (11.20 g) was hydrolysed essentially as described in General Procedure B to give the acid as a yellow solid (9.60 g, >99%).

m.p. 102°–104° C.

IR (KBr) $v_{max}$ 3001, 1691, 1510, 1251, 1176 cm$^{-1}$

UV (EtOH) $\lambda_{max}$ 275 (ε=55750), 232 (ε=30959), 204.5 (ε=65718) nm $^1$H (d$_6$-DMSO) δ12.85 (br s, CO$_2$H), 7.87 (d, J=9 Hz, 2ArH), 7.33 (d, J=9 Hz, 2ArH), 7.08 (d, J=8 Hz, 4ArH), 6.87 (d, J=8 Hz, 4ArH), 6.40 (s, OH), 3.73 (s, 6H, 2OMe) ppm

FDMS 364 (M+)

Analysis for C$_{22}$H$_{20}$O$_5$: Theory: C, 72.52; H, 5.53. Found: C, 72.09; H, 5.67.

Racemic 4-Carboxy-4'-methoxy-4''-methyltriphenylhydroxymethane

The corresponding oxazoline (5.50 g) was hydrolysed essentially as described in General Procedure B to give the acid as a solid (4.74 g, >99%).

IR (KBr) $v_{max}$ 3214, 1767, 1713, 1510, 1252 cm$^{-1}$ $^1$H (d$_6$-DMSO) δ12.20 (br s, CO$_2$H), 11.94 (br s, OH), 7.95 (d, J=8 Hz, 2ArH), 7.42 (d, J=8 Hz, 2 ArH), 7.15–7.04 (m, 6ArH), 6.85 (d, J=9 Hz, 2 ArH), 3.73 (s, OMe), 2.20 (s, Me) ppm.

FDMS for C$_{22}$H$_{20}$O$_4$ requires M 348; Found m/z 348 (85).

Racemic 4-Carboxy-4'-methoxytriphenylhydroxymethane

The corresponding oxazoline (800 mg) was hydrolysed essentially as described in General Procedure B to give the acid as a solid (640 mg, 93%).

m.p. 57°–62° C.

IR (CHCl$_3$) $v_{max}$ 3028, 3010, 1695, 1511, 1252 cm$^{-1}$ $^1$H (CDCl$_3$) δ8.04 (d, J=8 Hz, 2ArH), 7.46 (d, J=8 Hz, 2ArH), 7.34–7.25 (m, 5ArH), 7.14 (d J=8 Hz, 2ArH), 6.84 (d, J=8 Hz, 2ArH), 3.80 (s, OMe) ppm.

FDMS 334 (M+)

Analysis for C$_{21}$H$_{13}$O$_4$: Theory: C, 75.43; H, 5.43. Found: C, 75.68; H, 5.69.

Racemic 4-Carboxy-4'-methyltriphenylhydroxymethane

The corresponding oxazoline (18.0 g) was hydrolysed essentially as described in General Procedure B to give the acid as a yellow solid (13.35 g, 87%).

m.p. 91°–94° C.

IR (CHCl$_3$) $v_{max}$ 3380, 3020, 1692, 1282, 1009 cm$^{-1}$

UV (EtOH) $\lambda_{max}$ 247 (ε=12558), 203.5 (ε=45569) nm $^1$H (CDCl$_3$) δ8.03 (d, J=8 Hz, 2ArH), 7.44 (d, J=8 Hz, 2ArH), 7.35–7.23 (m, 5ArH), 7.13 (s, 4ArH), 2.36 (s, Me) ppm.

FDMS 318 (M+)

Analysis for C$_{21}$H$_{18}$O$_3$: Theory: C, 79.23; H, 5.70. Found: C, 78.87; H, 6.03.

4-Carboxytriphenylhydroxymethane

The corresponding oxazoline (8.00 g) was hydrolysed essentially as described in General Procedure B to give the acid as a solid (6.56 g, 96%).

m.p. 200°–202° C.

IR (CHCl$_3$) $v_{max}$ 3025, 3013, 1695, 1285 cm$^{-1}$ $^1$H (d$_6$-acetone) δ11.20 (br s, CO$_2$H), 7.99 (d, J=9 Hz, 2ArH), 7.50 (d, J=9 Hz, 2ArH), 7.37–7.25 (m, 10ArH), 2.80 (br s, OH) ppm.

FDMS 304 (M+)

Analysis for C$_{20}$H$_{16}$O$_3$: Theory: C, 78.93; H, 5.30. Found: C, 78.94; H, 5.37.

General Procedure C

To a stirred suspension of the carboxylic acid (18.1 mmol) and N-hydroxysuccinimide (18.1 mmol) in dry dichloromethane (100 ml) was added dicyclohexylcarbodiimide (21.7 mmol) at room temperature and the mixture was stirred for about 4 hours. The mixture was filtered and washed with dichloromethane. The filtrate was concentrated in vacuo to leave an oily residue which was further purified by column chromatography (gradient elution 25–50% ethyl acetate in hexanes) to give the active ester.

N-Succinimidyl-3-[bis-(4methoxyphenyl)hydroxymethyl]benzoate

The corresponding carboxylic acid (6.00 g) was coupled to N-hydroxysuccinimide (1.19 g) using dicyclohexylcarbodiimide (4.09 g), essentially as described in General Procedure C, to give the active ester as a yellow solid (4.23 g, 55.6%).

Tlc Rf(50% EtOAc/Hexanes) 0.23 m.p. 154°–156° C.

IR (CHCl$_3$) $v_{max}$ 3600, 3010, 1743, 1510, 1253, 1070 cm$^{-1}$ $^1$H (d$_6$-acetone) δ8.20 (br s, 1ArH), 8.05 (d, J=6 Hz, 1ArH), 7.68 (d, J=6 Hz, 1ArH), 7.57 (t, J=7 Hz, 1ArH), 7.21 (d, J=8 Hz, 4ArH), 6.88 (d, J=8 Hz, 4ArH), 3.80 (s, 6H, 2Me), 2.95 (s, 4H, 2CH$_2$), 2.80 (s, OH) ppm

FDMS 461 (M+)

Analysis for C$_{26}$H$_{23}$NO$_7$: Theory: C, 67.67; H, 5.02; N, 3.03. Found: C, 67.86; H, 5.22; N, 3.30.

N-Succinimidyl-4-[bis-(4methoxyphenyl)hydroxymethyl]benzoate

The corresponding carboxylic acid (728 mg) was coupled to N-hydroxysuccinimide (230 mg) using dicyclohexylcarbodiimide (454 mg), essentially as described in General Procedure C, to give the active ester as a white solid (880 mg, 95%).

Tlc Rf (5% MeOH/CHCl$_2$) 0.38 m.p. 184°–186° C.

IR (CHCl$_3$) $v_{max}$ 3600, 3050, 1744, 1570, 1254, 1179 cm$^{-1}$ $^1$H (CDCl$_3$) δ8.06 (d, J=8 Hz, 2ArH), 7.50 (d, J=8 Hz, 2ArH), 7.15 (d, J=8 Hz, 4ArH), 6.84 (d, J=8 Hz, 4ArH), 3.80 (s, 6 H, 2OMe), 2.87 (br s, 4H, 2CH$_2$) ppm

FDMS 461 (M+)

Analysis for C$_{26}$H$_{23}$NO$_7$: Theory: C, 67.67; H, 5.02; N, 3.03. Found: C, 67.94; H, 5.15; N, 3.24.

Racemic N-Succinimidyl-4-[4'-methoxyphenyl-4"methylphenyl-hydroxymethyl]benzoate The corresponding carboxylic acid (4.40 g) was coupled to N-hydroxysuccinimide (1.46 g) using dicyclohexylcarbodiimide (3.13 g), essentially as described in General Procedure C, to give the active ester as a yellow solid (2.85 g, 51%).

Tlc Rf (25% EtOAc/Hexanes) 0.25 m.p. 90°–94° C.

IR (CHCl$_3$) $v_{max}$ 3600, 3012, 1743, 1510, 1254, 1074 cm$^{-1}$ $^1$H (d$_6$-acetone) δ8.07 (d, J=8 Hz, 2ArH), 7.60 (d, J=8 Hz, 2ArH), 7.24–7.12 (m, 6ArH), 6.87 (d, J=8 Hz, 2ArH), 3.80 (s, 6H, 2OMe), 2.96 (s, 4H, 2CH$_2$), 2.31 (s, Me) ppm

FDMS 446 (M$^+$)

Analysis for C$_{21}$H$_{23}$NO$_6$: Theory: C, 70.10; H, 5.20; N, 3.14. Found: C, 69.84; H, 5.53; N, 3.34.

Racemic N-Succinimidyl-4-[4'-methoxyphenyl-phenylhydroxymethyl]benzoate

The corresponding carboxylic acid (6.00 g) was coupled to N-hydroxysuccinimide (2.07 g) using dicyclohexylcarbodiimide (4.46 g), essentially as described in General Procedure C, to give the active ester as a solid (5.98 g, 77%).

Tlc Rf (50% EtOAc/Hexanes) 0.43 m.p. 85°–90° C.

IR (CHCl$_3$) $v_{max}$ 3600, 3010, 1744, 1254 cm$^{-1}$ $^1$H (CDCl$_3$) δ8.08 (d, J=8 Hz, 2ArH), 7.52 (d, J=9 Hz, 2ArH), 7.37–7.23 (m, 5ArH), 7.14 (d, J=10 Hz, 2ArH), 6.86 (d, J=10 Hz, 2ArH), 3.82 (s, OMe), 2.90 (s, 4H, 2CH$_2$) ppm

FDMS 431 (M+)

Analysis for C$_{25}$H$_{21}$NO$_7$: Theory: C, 69.60; H, 4.91; N, 3.25. Found: C, 69.36; H, 5.04; N, 3.29.

Racemic N-Succinimidyl-4-[4-methylphenyl-phenylhydroxymethyl]benzoate

The corresponding carboxylic acid (13.20 g) was coupled to N-hydroxysuccinimide (4.77 g) using dicyclohexylcarbodiimide (10.27 g), essentially as described in General Procedure C, to give the active ester as a solid (15.65 g, 91%).

Tlc Rf (50% EtOAc/Hexanes) 0.38
m.p. 156°–158° C.
IR (KBr) $\nu_{max}$ 3467, 1771, 1731, 1212, 996 cm$^{-1}$
UV (EtOH) $\lambda_{max}$ 249 ($\epsilon$=18105), 206 ($\epsilon$=48790) nm
$^1$H (d$_6$-DMSO) $\delta$8.03 (d, J=9 Hz, 2ArH), 7.50 (d, J=9 Hz, 2ArH), 7.36–7.26 (m, 3ArH), 7.23–7.19 (m, 2ArH), 7.16–7.06 (br q, J=8 Hz, 4ArH), 2.89 (s, 4H, 2CH$_2$), 2.30 (s, Me) ppm
FDMS 415 (M+)
Analysis for C$_{25}$H$_{21}$NO$_5$: Theory: C, 72.28; H, 5.10; N, 3.37. Found: C, 71.95; H, 5.26; N, 4.06.

N-Succinimidyl-4-[bis-phenyl-hydroxymethyl]benzoate

The corresponding carboxylic acid (5.50 g) was coupled to N-hydroxysuccinimide (2.08 g) using dicyclohexylcarbodiimide (4.48 g), essentially as described in General Procedure C, to give the active ester as a solid (6.88 g, 95%).

Tlc Rf (50% EtOAc/Hexanes) 0.29
m.p. 151°–153° C.
IR (CHCl$_3$) $\nu_{max}$ 3030, 1774, 1742, 1448, 1374, 1256, 1202, 1046, 996 cm$^{-1}$
$^1$H (d$_6$-acetone) $\delta$8.08 (d, J=8 Hz, 2ArH), 7.50 (d, J=8 Hz, 2ArH), 7.39–7.30 (m, 6ArH), 7.30–7.22 (m, 4ArH), 2.90 (br s, 4H, 2CH$_2$) ppm
FDMS 401 (M+)
Analysis for C$_{24}$H$_{19}$NO$_5$: Theory: C, 71.10; H, 4.77; N, 3.49. Found: C, 72.10; H, 5.00; N, 3.69.

General Procedure D

The appropriate carbinol (4.98 mmol) was dissolved in freshly distilled acetyl chloride (25 ml) at room temperature under a dry nitrogen atmosphere. The resulting solution was heated at reflux for 5–24 hours, cooled to room temperature and concentrated in vacuo to ~⅓ of its original volume. Dry diethyl ether (20 ml) was added to form a precipitate, which was collected by filtration and washed with further dry diethyl ether and dried under vacuum to give the chloride as a solid. In those cases where product did not precipitate with diethyl ether, the reaction solution was concentrated in vacuo to dryness and azeotroped with dry dichloromethane (5×10 ml) to give the chloride as a solid.

N-Succinimidyl-3-[bis-(4-methoxyphenyl)chloromethyl]benzoate

The corresponding carbinol (2.00 g) was heated in acetyl chloride essentially as described in General Procedure D to provide the chloride as a reddish-orange solid (1.52 g, 73%).

m.p. 165°–167° C.
IR (CHCl$_3$) $\nu_{max}$ 1774, 1744, 1510, 1255, 1179, 1070 cm$^{-1}$
$^1$H (CDCl$_3$) $\delta$8.10 (d, J=10 Hz, 1ArH), 8.05 (s, 1ArH), 7.62 (d, J=10 Hz, 1ArH), 7.50–7.42 (m, 1ArH), 7.12 (d, J=10 Hz, 4ArH), 6.82 (d, J=10 Hz, 4ArH), 3.80 (s, 6H, 2OMe), 2.90 (br s, 4H, 2CH$_2$) ppm
FAB MS 444.2 (M-Cl$^+$)
Analysis for C$_{26}$H$_{22}$ClNO$_6$: Theory: C, 65.07; H, 4.62; N, 2.92; Cl, 7.09. Found: C, 64.86; H, 2.90; N, 2.90; Cl, 7.09.

N-Succinimidyl-4-[bis-(4-methoxyphenyl)chloromethyl]benzoate

The corresponding carbinol (420 mg) was heated in acetyl chloride essentially as described in General Procedure D to provide the chloride as a white crystalline solid (320 mg, 73%).

m.p. 202°–203° C.
IR (CHCl$_3$) $\nu_{max}$ 1774, 1744, 1510, 1255, 1071 cm$^{-1}$
$^1$H (CDCl$_3$) $\delta$8.80 (d, J=9 Hz, 2ArH), 7.46 (d, J=9 Hz, 2ArH), 7.14 (d, J=9 Hz, 4ArH), 6.85 (d, J=9 Hz, 4ArH), 3.84 (s, 6H, 2OMe), 2.93 (br s, 2CH$_2$) ppm
FAB MS 444.2 (M-Cl$^+$)
Analysis for C$_{26}$H$_{22}$ClNO$_6$: Theory: C, 65.07; H, 4.62; N, 2.66; Cl, 7.39. Found: C, 65.23; H, 4.63; N, 2.66; Cl, 7.58.

Racemic N-Succinimidyl-4-[4'-methoxyphenyl-4''methylphenyl-chloromethyl]benzoate The corresponding carbinol (1.00 g) was heated in acetyl chloride essentially as described in General Procedure D to provide the chloride as a white solid (843 mg, 81%).

m.p. 194°–196° C.
IR (CHCl$_3$) $\nu_{max}$ 1774, 1744, 1609, 1510, 1256, 1182, 1070, 996 cm$^{-1}$
$^1$H (d$_6$-DMSO) $\delta$8.04 (d, J=8 Hz, 2ArH), 7.47 (d, J=8 Hz, 2ArH), 7.15–7.06 (m, 6ArH), 6.88 (d, J=8 Hz, 2ArH), 3.71 (s, OMe), 2.90 (s, 4H, 2CH$_2$), 2.28 (s, Me) ppm
FAB MS 428.2 (M-Cl$^+$)
Analysis for C$_{26}$H$_{22}$ClNO$_5$: Theory: C, 67.31; H, 4.78; N, 3.02; Cl, 7.64. Found: C, 67.57; H, 4.75; N, 3.05; Cl, 7.75.

Racemic N-Succinimidyl-4-[4'-methoxyphenyl-phenylchloromethyl]benzoate

The corresponding carbinol (2.00 g) was heated in acetyl chloride essentially as described in General Procedure D to provide the chloride as a white solid (1.15 g, 55%).

m.p. 161°–163° C.
IR (CHCl$_3$) $\nu_{max}$ 1774, 1744, 1511, 1253, 1071, 996 cm$^{-1}$
$^1$H (CDCl$_3$) $\delta$8.04 (d, J=8 Hz, 2ArH), 7.52 (d, J=8 Hz, 2ArH), 7.37–7.18 (m, 5ArH), 7.10 (d, J=9 Hz, 2ArH), 6.90 (d, J=9 Hz, 2ArH), 3.74 (s, OMe), 2.90 (s, 4H, 2CH$_2$) ppm
FAB MS 450 (M$^+$)
Analysis for C$_{25}$H$_{20}$ClNO$_5$: Theory: C, 66.74; H, 4.48; N, 3.11; Cl, 7.88. Found: C, 67.01; H, 4.50; N, 3.12; Cl, 7.72.

Racemic N-Succinimidyl-4-[4-methylphenyl-phenylchloromethyl]benzoate

The corresponding carbinol (2.50 g) was heated in acetyl chloride essentially as described in General Procedure D to provide the chloride as a pale yellow solid (2.35 g, 90%).

IR (CHCl$_3$) $\nu_{max}$ 1775, 1744, 1257, 1201, 1071, 996 cm$^{-1}$.
$^1$H (d$_6$-DMSO) $\delta$8.04 (d, J=8 Hz, 2ArH), 7.50 (d, J=8 Hz, 2ArH), 7.36–7.25 (m, 2ArH), 7.25–7.17 (m, 3ArH), 7.12 (q, J=8 Hz, 4ArH), 2.88 (s, 4H, 2CH$_2$), 2.28 (s, Me) ppm
FAB MS 415 (M-Cl+OH$^+$)
Analysis for C$_{25}$H$_{20}$ClNO$_4$: Theory: C, 69.21; H, 4.65; N, 3.23. Found: C, 69.50; H, 4.79; N, 3.47.

N-Succinimidyl-4-[bis-phenyl-chloromethyl]benzoate

The corresponding carbinol (2.00 g) was heated in acetyl chloride essentially as described in General Procedure D to provide the chloride as a white solid (1.20 g, 57%).

m.p. 173°–175° C.

IR (CHCl$_3$) $\nu_{max}$ 1775, 1744, 1071, 997 cm$^{-1}$ $^1$H (CDCl$_3$) δ8.08 (d, J=8 Hz, 2ArH), 7.45 (d, J=8 Hz, 2Ar H), 7.38–7.29 (m, 4 ArH), 7.29–7.18 (m, 4ArH), 2.92 (s, 4H, 2CH$_2$) ppm

FDMS 419 (M$^+$)

Analysis for C$_{24}$H$_{18}$ClNO$_4$: Theory: C, 68.66; H, 4.32; N, 3.34; Cl, 8.44. Found: C, 68.75; H, 4.36; N, 3.26; Cl, 8.55.

EXAMPLE 2

Assembly Of The Linker-Drug Moiety (136 mg) and collidine (70 µl) for 20 minutes, essentially as described in General Procedure E, to give the product as a white solid (190 mg, 77%).

Tlc Rf (10% MeOH/CH$_2$Cl$_2$) 0.42

IR (KBr) $\nu_{max}$ 3379, 1740, 1606, 1253, 1072 cm$^{-1}$

UV (EtOH) $\lambda_{max}$ 278 (ε=9970.5), 225.5 (ε=32651), 103.5 (ε=50143) nm $^1$H (d$_6$-DMSO) δ (8.07 (s, 1ArH), 7.90–7.77 (m, 2Ar H), 7.88 (s, H8), 7.50 (t, J=9 Hz, 1ArH), 7.27 (dd, J=4 Hz and 10 Hz, 4ArH), 6.95 (s, NH), 6.80 (dd, J=6, 10 Hz, 4Ar H), 6.74 (br s, NH$_2$), 6.24 (d, J=6 Hz, 3'OH), 5.60–5.44 (m, H1'), 5.19 (t, J=4 Hz, 5'OH), 4.41–4.23 (m, H3'), 3.82–3.54 (m, 3H, H4'5'5'), 3.70 (s, 6H, 2OMe), 2.84 (s, 4H, 2CH$_2$) ppm

FDMS 746 (M$^+$)

Analysis for C$_{36}$H$_{33}$F$_2$N$_7$O$_9$: Theory: C, 57.99; H, 4.40; N, 13.15. Found: C, 57.81; H, 4.73; N, 12.89.

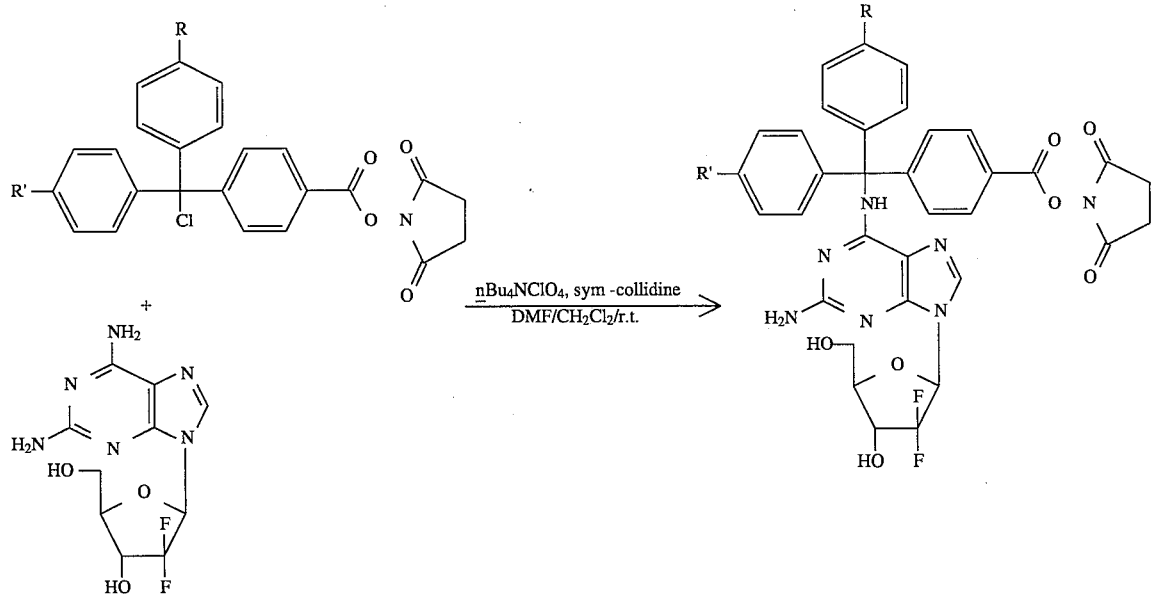

General Procedure E

2-Amino-2'-deoxy-2',2'-difluoroadenosine (ADDFA) (0.331 mmol) was dissolved in a solvent mixture of dry dimethylformamide:dichloromethane (1:1; 6 ml) at room temperature and then tetra-n-butylammonium perchlorate (TBAPC) (0.397 mmol) and dry collidine (0.497 mmol) were added. The solution was stirred for 5 minutes and then trityl chloride (0.331 mmol) was added portionwise over 3 minutes. The resulting solution was stirred at room temperature under dry nitrogen until all the starting material was consumed (as determined by thin layer chromatography). The crude reaction solution was diluted with ethyl acetate (1 volume) and directly applied onto a silica column and purified by chromatography (gradient elution EtOAc→ 5–20% iPrOH/EtOAc) to give the desired product.

N-Succinimidyl-3-[bis-(4-methoxyphenyl)-6-N-[2-amino-9-(2'-deoxy-2',2'-difluoro-β-ribofuranosyl)purinyl]methyl]benzoate 2-Amino-2'-deoxy-2',2'-difluoroadenosine (100 mg) was reacted at with N-succinimidyl-3-[bis-(4-methoxyphenyl)chloromethyl]benzoate (159 mg) in the presence of TBAPC N-Succinimidyl-4-[bis-(4-methoxyphenyl)-6-N-[2-amino-9-(2'-deoxy-2',2'-difluoro-β-ribofuranosyl)purinyl]methyl]benzoate 2-Amino-2'-deoxy-2',2'-difluoroadenosine (100 mg) was reacted at with N-succinimidyl-4-[bis-(4-methoxyphenyl)chloromethyl]benzoate (159 mg) in the presence of TBAPC (136 mg) and collidine (70 µl) for 30 minutes, essentially as described in General Procedure E, to give the product as a white powder (232 mg, 94%).

Tlc Rf (10% MeOH/CH$_2$Cl$_2$) 0.22

IR (KBr) $\nu_{max}$ 3372, 2933, 1741, 1608, 1510, 1072 cm$^{-1}$

UV (EtOH) $\lambda_{max}$ 261 (ε=22597), 226.5 (ε=43631) nm $^1$H (d$_6$-DMSO) δ7.95 (d, J=10 Hz, 2ArH), 7.87 (s, H8), 7.62 (d, J=8 Hz, 2ArH), 7.27 (d, J=8 Hz, 4ArH), 6.91 (s, N H), 6.80 (dd, J=3, 10 Hz, 4ArH), 6.72 (br s, NH$_2$), 6.25 (d, J=6 Hz, 3'OH), 5.65–5.44 (m, H1'), 5.19 (t, J=6 Hz, 5'O H), 4.44–4.26 (m, H3'), 3.83–3.63 (m, 3H, H4'5'5'), 3.70 (s, 6H, 2OMe), 2.85 (s, 4H, 2CH$_2$) ppm

FDMS 746 (M$^+$)

Analysis for C$_{36}$H$_{33}$F$_2$N$_7$O$_9$: Theory: C, 57.99; H, 4.46; N, 13.15. Found: C, 58.05; H, 4.82; N, 12.80.

N-Succinimidyl-4-[4-methoxyphenyl-4'-methylphenyl-6-N-[2-amino-9-(2'-deoxy-2',2'-difluoro-β-ribofuranosyl)purinyl]methyl]benzoate 2-Amino-2'-deoxy-2',2'-difluoroadenosine (200 mg) was reacted at with N-succinimidyl-4-[4'-methoxyphenyl-4"methylphenyl-chloromethyl]benzoate (307 mg) in the presence of TBAPC (271 mg) and collidine (132 µl) for about two hours, essentially as described in General Procedure E, to give the product as a yellow solid (404 mg; 84%).
[Mixture of diastereomers]
Tlc Rf (10% MeOH/CH$_2$Cl$_2$) 0.49
IR (KBr) $v_{max}$ 3376, 1772, 1740, 1606, 1256, 1073 cm$^{-1}$
UV (EtOH) $\lambda_{max}$ 259 (ε=26254) nm
$^1$H (d$_6$-DMSO) δ7.95 (d, J=8 Hz, 2ArH), 7.88 (s, H8), 7.62 (d, J=10 Hz, 2ArH), 7.30–7.22 (m, 4ArH), 7.05 (dd, J=2, 8 Hz, 2ArH), 6.92 (s, NH), 6.79 (dd, J=8, 10 Hz, 2Ar H), 6.74 (br s, NH$_2$), 6.25 (d, J=6 Hz, 3'OH), 5.64–5.43 (m, H1'), 5.20 (t, J=6 Hz, 5'OH), 4.44–4.24 (m, H3'), 3.84–3.54 (m, 3H, H4'5'5'), 3.72 (s, OMe), 2.87 (s, 4H, 2CH$_2$), 2.23 (s, Me) ppm
FDMS 730 (M$^+$)
Analysis for C$_{36}$H$_{33}$F$_2$N$_7$O$_8$: Theory: C, 59.26; H, 4.56; N, 13.44. Found: C, 59.20; H, 4.84; N, 13.48.

N-Succinimidyl-4-[(4-methoxyphenyl)phenyl]-6-N-[2-amino-9-(2'-deoxy-2',2'-difluoro-β-ribofuranosyl)purinyl]methyl]benzoate 2-Amino-2'-deoxy-2',2'-difluoroadenosine (302 mg) was reacted at with N-succinimidyl-4-[4'-methoxyphenylphenylchloromethyl]benzoate (450 mg) in the presence of TBAPC (271 mg) and collidine (160 µl) for 2 hours, essentially as described in General Procedure E, to give the product as a pale yellow powder (493 mg; 70%).
[Mixture of diastereomers]
Tlc Rf (10% MeOH/CH$_2$Cl$_2$) 0.34
IR (KBr) $v_{max}$ 3374, 1739, 1607, 1511, 1256, 1207, 1073 cm$^{-1}$
$^1$H (d$_6$-DMSO) δ7.95 (d, J=8 Hz, 2ArH), 7.87 (s, H8), 7.64 (d, J=10 Hz, 2ArH), 7.38 (d,J=8 Hz, 2ArH), 7.30–7.13 (m, 5ArH), 7.02 (s, NH), 6.80 (dd, J=2, 7 Hz, 2ArH), 6.75 (br s, NH$_2$), 6.25 (d, J=6 Hz, 3'OH), 5.60–5.44 (m, H1'), 5.20 (t, J=6 Hz, 5'OH), 4.42–4.26 (m, H3'), 3.82–3.52 (m, 3H, H4'5'5'), 3.70 (s, OMe), 2.87 (s, 4H, 2CH$_2$) ppm
FDMS for C$_{35}$H$_{31}$F$_2$N$_7$O$_8$ requires M 716; Found m/z 716.

N-Succinimidyl-4-[4-methylphenyl-phenyl)-6-N-[2-amino-9-(2'-deoxy-2',2'-difluoro-β-ribofuranosyl)purinyl]methyl]benzoate 2-Amino-2'-deoxy-2',2'-difluoroadenosine (200 mg) was reacted with N-succinimidyl-4-[4-methylphenyl-phenylchloromethyl]benzoate (287 mg) in the presence of TBAPC (271 mg) and collidine (132 µl) for about 3 hours, essentially as described in General Procedure E, to give the product as a white solid (604 mg, 65%).
[Mixture of Diastereomers]
Tlc Rf (10% MeOH/CH$_2$Cl$_2$) 0.50
IR(KBr) $v_{max}$ 3379, 1773, 1740, 1606, 1467, 1205, 1073 cm$^{-1}$
$^1$H (d$_6$-DMSO) δ7.96 (br d,J=6 Hz, 2ArH), 7.86 (s, H8), 7.64 (d, J=10 Hz, 2ArH), 7.42–7.35 (m, 2ArH), 7.30–7.12 (m, 5ArH), 7.10–7.02 (m, 2ArH), 7.14 (s, NH), 6.76 (br s, NH$_2$), 6.26 (d, J=7 Hz, 3'OH), 5.58–5.45 (m, 3H, H4'5'5'), 2.87 (br s, 4H, 2CH$_2$), 2.24 (s, Me) ppm
FDMS 699 (M+)

Analysis for C$_{35}$H$_{31}$F$_2$N$_7$O$_8$: Theory: C, 60.08; H, 4.47; N, 14.01. Found: C, 59.89; H, 4.30; N, 13.82.

N-Succinimidyl-4-[bis-phenyl-6-N-[2-amino-9-(2'-deoxy-2',2'-difluoro-β-ribofuranosyl)purinyl]methyl]benzoate 2-Amino-2'-deoxy-2',2'-difluoroadenosine (302 mg) was reacted with N-succinimidyl-4-[bis-phenyl-chloromethyl]benzoate (402 mg) in the presence of TBAPC (401 mg) and collidine (160 µl) for about one hour, essentially as described in General Procedure E, to give the product as a white solid (391 mg, 57%).
Tlc Rf (10% MeOH/CH$_2$Cl$_2$) 0.27
IR (CHCl$_3$) $v_{tmax}$ 3379, 1772, 1739, 1607, 1467, 1207, 1073 cm$^{-1}$
UV (EtOH) $\lambda_{max}$ 259 (ε=24723) nm
$^1$H (d$_6$-DMSO) δ7.97 (d, J=9 Hz, 2ArH), 7.88 (s, H8), 7.66 (d, J=9 Hz, 2ArH), 7.42–7.36 (m, 4ArH), 7.28–7.10 (m, 6ArH), 7.04 (s, NH), 6.76 (br s, NH$_2$), 6.15 (d, J=6 Hz, 3'O H), 5.60–5.44 (m, H1'), 5.20 (t, J=6 Hz, 5'OH), 4.40–4.24 (m, H3'), 3.80–3.54 m, 3H, H4'5'5'), 2.88 (s, 4H, 2CH$_2$) ppm
FDMS for C$_{34}$H$_{29}$F$_2$N$_7$O$_7$ requires M 685; Found m/z 685 (100).

5'-OH Tritylation

N-Succinimidyl-4-[bis-(4-methoxyphenyl)-5'-O-[2,6-di-(pivaloylamino)-9-(2'-deoxy-2'2'-difluoro-β-D-ribofuranosyl)purinyl]methyl]benzoate Protected nucleoside (300 mg) was dissolved in dry dichloromethane (14 ml) at room temperature and then tetra-n-butylammonium perchlorate (300 mg) and dry collidine (260 µl) were added. The solution was stirred for 5 minutes and then N-succinimidyl-4-[bis-(4-methoxyphenyl)chloromethyl]benzoate (421 mg) was added portionwise over 3 minutes. The resultant pink solution was stirred at room temperature under nitrogen for 4 hours until all the starting nucleoside had been consumed (as determined by thin layer chromatography). The crude reaction solution was diluted with ethyl acetate (1 volume) and directly applied onto a silica column for purification by chromatography (gradient elution EtOAc-5–10% iPrOH/EtOAc) to give the product as a yellow glass (270 mg; 47%)
Tlc Rf (EtOAc ) 0.95
IR (KBr) $v_{max}$ 3425,2967,1743,1254,1074 cm–1
UV (EtOH) $\lambda_{max}$ 284.5 (ε=19076), 264 (ε=19683), 235.5 (ε=57148), 203.5 (ε=81780) nm
$^1$H (CDCl$_3$) δ9.00 (s, NH), 8.68 (s, NH), 8.08 (s, H8), 7.85 (d, J=9 Hz, 2ArH), 7.63 (d, J=8 Hz, 2ArH), 7.34 (d, J=9 Hz, 2ArH), 7.25 (d, J=9 Hz, 2ArH), 6.80 (d, J=8 Hz, 4ArH), 6.32–6.28 (m, H1'), 5.13–5.05 (m, H3'), 4.38–4.32 (m, H4'), 3.80 (s, OMe), 3.78 (s, OMe), 3.67–3.62 (m, H5'), 3.47–3.42 (m, H5'), 2.92 (br s, 4H, 2CH$_2$), 1.40 (s, 9H, C(Me)$_3$), 1.24 (s, 9H, C(Me)$_3$) ppm
FDMS for C$_{46}$H$_{49}$N$_7$O$_{11}$F$_2$ requires M914; Found m/z 914 (20).

N-Isoprpyl-4-[bis-(4-methoxyphenyl)-5'-O-[2,6-di-(pivaloylamino)-9-(2'-deoxy-2'2'-difluoro-β-D-ribofuranosyl)purinyl]methyl]benzamide To a stirred solution of active ester (70 mg) in dry dichloromethane (2 ml) was added neat isopropylamine (0.15 ml). The solution formed an immediate precipitate and was stirred for a further 1 hour and then filtered and concentrated to give a solid. The crude product was further purified by column chromatography (gradient elution $CH_2Cl_2$-5% $MeOH/CH_2Cl_2$) to provide the amide as a white solid. (62 mg, 94%)

Tlc Rf (5% $MeOH/CHCl_2$) 0.30

IR (KBr) $v_{max}$ 3424,2972,1713,1609,1510,1440,1252,1176,1068 $cm^{-1}$

UV (EtOH) $\lambda_{max}$ 283.5 ($\epsilon$=15390), 235.5 ($\epsilon$=57497), 204 ($\epsilon$=80562) nm $^1$H (CDCl3) $\delta$9.27 (br s, N$\underline{H}$), 8.83 (br s, N$\underline{H}$), 8.16 (s, $\underline{H}$8), 7.58 (q, J=9 Hz, 4Ar$\underline{H}$), 7.34–7.30 (m, 4Ar$\underline{H}$), 7.0 (br d, N$\underline{H}$), 6.80 (d, J=9 Hz, 4Ar$\underline{H}$), 6.65–6.50 (m, $\underline{H}$1'), 6.00 (d, J=8 Hz, 3'O$\underline{H}$), 4.87–4.81 (m, H3'), 4.40–4.35 (m, $\underline{H}$4'), 4.35–4.20 (m, C$\underline{H}$), 3.77 (br s, 6H, 2OMe), 3.48 (br s, 2H, $\underline{H}$5'5'), 1.40 (s, 9H, C(Me)$_3$), 1.26 (s, 9H, C(Me)$_3$), 1.22 (d, J=6 Hz, 2Me) ppm FDMS for $C_{45}H_{53}F_2N_7O_8$ requires $\underline{M}$858;Found m/z 858 (85), 470 (35), 388 (100)

N-Isoprpyl-4-[bis-(4-methoxyphenyl)-5'-O-[2,6-diamino-9-(2'-deoxy-2'2'-difluoro-β-D-ribofuranosyl)purinyl]benzamide Freshly prepared sodium methoxide (0.35 mM) was added to a dry solution of protected nucleoside (60 mg) in dry methanol (1.0 ml) at room temperature under a dry nitrogen atmosphere. The solution was heated at reflux for 3 hours, and then concentrated in vacuo to give a solid residue which was diluted with water (5 ml) and extracted with ethyl acetate (3×5 ml). The combined organics were dried with sodium sulphate and then concentrated to give the product as a white solid (47 mg, 98%)

Tlc Rf (5% $MeOH/CHCl_2$) 0.46

IR (KBr) $v_{max}$ 3376, 1609, 1509, 1251, 1176, 1082, 1034 $cm^{-1}$

UV (EtOH) $\lambda_{max}$ 252 ($\epsilon$=21925), 204.5 ($\epsilon$=76124) nm $^1$H (d$_6$-acetone) $\delta$7.80 (s, $\underline{H}$8), 7.78 (d, J=8 Hz, 2Ar$\underline{H}$), 7.55 (d, J=6 Hz, 2Ar$\underline{H}$), 7.40 (br s, NH), 7.36 (dd, J=2 Hz, J=8 Hz, 4Ar$\underline{H}$), 6.90 (dd, J=4 Hz, J=12 Hz, 4Ar$\underline{H}$), 6.26–6.14 (m, 3H, N$\underline{H}$,$\underline{H}$1'), 5.47–5.32 (m, 3H, NH$_2$, O $\underline{H}$), 4.88–4.74 (m, $\underline{H}$3'), 4.30–4.12 (m, 2H, C$\underline{H}$,$\underline{H}$4'), 3.80 (s, 6H, 2OMe), 3.60–3.44 (m, H5'5'), 1.22 (d, J=7 Hz, 6H, 2Me) ppm FDMS for $C_{35}H_{37}N_7O_6F_2$ requires $\underline{M}$689; Found m/z 689 (100); 388 (85)

EXAMPLE 3

Attachment Of The Drug-Linker Moiety To The Antibody

In conformity with the preceding Examples, reaction schemes and a narrative section embellishing the reaction scheme are provided below.

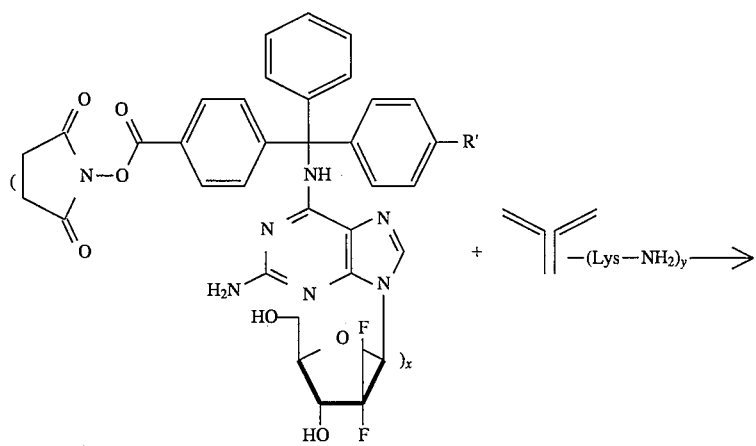

where x = Molar Input Ratio (MIR)

-continued

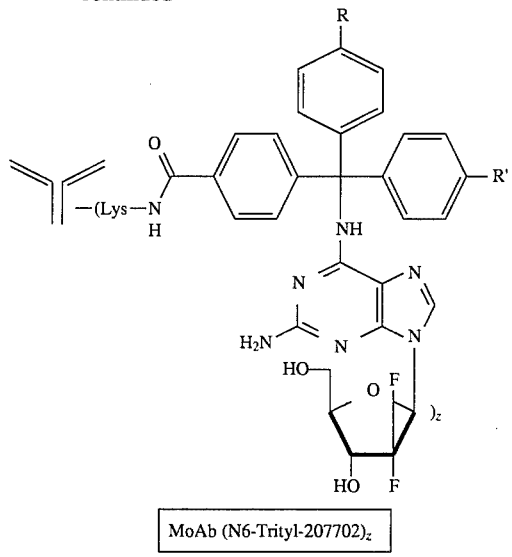

where z = Conjugation Ratio (CR)

(i) 0.1M Borate buffer pH ~8.6, 7.5% DMF, r.t., 1 hr 0.1M Borate buffer

Boric acid 12.37 g) was dissolved in deionized water (2 L) and then the pH was adjusted to 8.60 using 50% aqueous sodium hydroxide to give a 0.1M borate buffer solution.
PBS—Phosphate Buffered Saline Dulbecco's PBS powder (GIBCO) was dissolved in deionized water (1 L) to give a 0.1M solution of PBS (pH=7.4).
Exhaustive Dialysis Monoclonal antibody (purified on Protein-A column) was dialysed in a molecular porous membrane (M.W. cutoff= 12000–14000,2 ml/cm) tubing against 0.1M borate buffer (100×volume, pH 8.60) at 4° C. for 20 to 30 hours. The resulting solution was sterile filtered and the protein concentration determined.

Concentration in a stirred-cell using disc membranes (M.W. cutoff 30,000 pre-soaked in water to remove azide) at 55 psi/$N_2$ pressure
Solvents All solvents were filtered through 0.22 μm membrane and then throughly de-gassed with nitrogen.

U.V. measurements were performed on a spectrophotometer. A 1 cm path length U.V. cell was used to measure the absorbance of the product diluted in PBS /df=dilution factor) at $\lambda_{max}$ (protein)=279 nm and $\lambda_{max}$ (drug-linker)=254 nm or 263 nm.
Conjugation Ratio (CR) determination Protein was diluted with PBS (df=20) and absorbance measured at 279 nm (average of 10 readings). The concentration of protein was determined using the formulae:

$$[Ab]=(A_{279} \times df)/1.43$$

where $A_{279}$=1.43 at 1 mg/ml for monoclonal antibodies and the drug concentration from the Beer-Lambert Law:

$$\epsilon = A/cl$$

where $\epsilon$ is the molar absorptivity (molecular extinction coefficient)

l is the path length of the sample (cm)

c is the concentration of solute (mol $dm^{-3}$)

A is the Absorbance of the solution (optical density, O.D.)

The Conjugation Ratio (CR) is defined as the number of moles of drug per mole of antibody i.e.:

$$CR = \frac{\text{Moles of drug}}{\text{Moles of antibody}}$$

To a stirred 0.1M Borate buffer (pH 8.64) solution of protein (1.442 ml of 10.4 mg/ml=15 mg; $1.00 \times 10^{-7}$M) was slowly added to a solution of N6-Trityl-DDFA active ester (0.55 mg; $8.00 \times 10^{-7}$M) in re-distilled N,N-dimethylformamide (117 μl) at room temperature. The reaction mixture turned cloudy and was allowed to stir for a further 1 hour. The clear solution was centrifuged at 2000×G for 10 minutes and the supernatant then purified on a G-25 SEPHADEX® (medium) HR 16/50 column (pre-equilibrated with phosphate buffered saline). The product was eluted with phosphate buffered saline and the fractions containing product combined and concentrated. The final product was sterile filtered and then analysed by SUPEROSE 12® column for agggregate content. The conjugation ratio, protein and drug concentrations, and protein yield were determined from the U.V. spectrum of the conjugate.

The conjugation ratios, yields, and $IC_{50}$s of immunoconjugates prepared in accordance with the procedure set forth above are provided in Table III. Table III uses several abbreviations which are defined as follows. The terms D612, COL-1, CC83, and CC49 refer to specific murine monoclonal antibodies which are described in detail in the Antibody section of the Detailed Description. The N6-linker-drug linker series is defined in Table II and further described in the narrative section of Example 2. "CR#" is an abbreviation for conjugation ratio. "MIR" refers to the molar input ratio of the linker-drug relative to the antibody. $IC_{50}$'s were determined in cytotoxicity assays wherein the uptake of tritiated leucine by LS-174T human colon carcinoma over a 48 hour period was used determine the concentration of the immunoconjugate required to suppress leucine uptake by treated cells relative to untreated cells by 50%.

| MoAb-(N6-Linker-ADDFA) | CR# (MIR = 8) | YIELD# (%) | IC$_{50}$* (μg/ml) |
|---|---|---|---|
| ADDFA | | | 0.260 |
| D612 | | | |
| T | 4.33 | 77 | >5 |
| MMT | 5.32 | 75 | 1.50 |
| DMT | 5.45 | 62 | 0.288 |
| m-DMT | 4.43 (MIR = 5) | 79 | 0.185 |
| COL-1 | | | |
| T | 4.48 | 74 | 10 |
| MeT | 5.72 | 61 | 6.04 |
| MMT | 5.19 | 73 | 4.94 |
| MMeT | 7.49 | 44 | 2.71 |
| DMT | 7.66 | 31 | 0.27 |
| m-DMT | 6.44 | 52 | 0.352 |
| CC83 | | | |
| T | 5.04 | 86 | >6.50 |
| MMT | 6.57 | 80 | 5.70 |
| DMT | 5.77 | 86 | 0.350 |
| m-DMT | 7.04 | 79 | 0.390 |
| CC49 | | | |
| T | 5.27 | 88 | >7 |
| MMT | 7.53 | 84 | 2.90 |
| DMT | 6.82 | 64 | 0.510 |
| m-DMT | 7.36 | 94 | 0.700 |

Determined by U.V. Spectroscopy (Beer-Lambert Law)
*Cytotoxicity assay performed on LS 174T Human Colon Carcinoma cells (48 hours incubation $^3$H-Leucine uptake)

EXAMPLE 4

A. Preparation of the Isopropylamide Derivatives

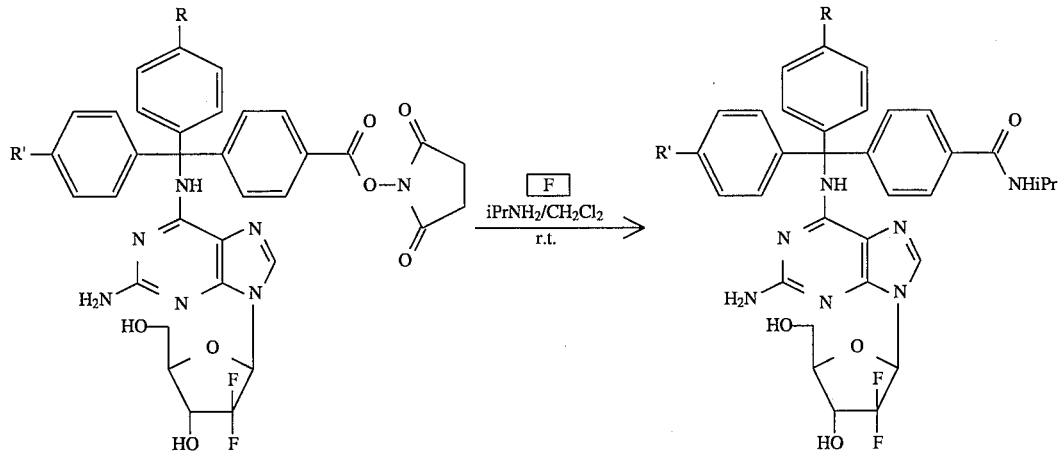

General Procedure F

To a stirred solution of active ester (0.147 mM) in dry dichloromethane (3 ml) was added freshly redistilled, dry isopropylamine (0.734 mM). The solution formed an immediate precipitate and was stirred for a further 1 hour, filtered and concentrated to give a solid. The crude product was purified by cloumn chromatography (gradient elution CH$_2$Cl$_2$→10% MeOH/CH$_2$Cl$_2$) to furnish the desired amide.

N-Isopropyl-3-[bis-(4-methoxyphenyl)-6-N-[2-amino-9-(2'-deoxy-2',2'-difluoro-β-ribofuranosyl)purinyl]methyl]benzamide Active ester (30 mg) was reacted with isopropylamine, according to General Procedure F, to give the amide as a white solid (20.6 mg; 74%)

TLC Rf (10% MeOH/CH$_2$Cl$_2$) 0.35

IR (CHCl$_3$) ν$_{max}$ 3365, 2931, 1608, 1509, 1465, 1251, 1178, 1034, 830, 592 cm$^{-1}$ U.V. (EtOH) λ$_{max}$ 277.5 (ε=14006), 224.5 (ε=47152), 205 (ε=70300) nm $^1$H NMR (d$_6$-Acetone) δ8.03 (s, ArH), 7.83 (s, H8), 7.65 (d, J=8 Hz, ArH), 7.52 (d, J=8 Hz, ArH), 7.48 (d, J=9 Hz, Ar H), 7.26 (d, J=8 Hz, 4ArH), 6.80 (d, J=8 Hz, 4ArH), 6.35 (s, NH), 6.20 (br s, NH$_2$), 5.76–5.71 (m, H1'), 5.55 (br s, 3'O H), 4.82 (br s, 5'OH), 4.62–4.57 (m, H3'), 4.20–4.12 (m, CH), 3.93–3.74 (m, 3H, H4'5'5'), 3.74 (s, 6H, 2OMe), 1.14 (d, J=6.6 Hz, 6H, 2Me) ppm FDMS for C$_{35}$H$_{37}$N$_7$O$_6$F$_2$ requires M690; Found m/z 690 (100)

N-Isopropyl-4-[bis-(4-methoxyphenyl)-6-N-[2-amino-9-(2'-deoxy-2',2'-difluoro-β-ribofuranosyl)purinyl]methyl]benzamide Active ester (60 mg) was reacted with isopropylamine, according to General Procedure F, to give the amide as a white soild (38 mg; 69%)

Tlc Rf (10% MeOH/CH$_2$Cl$_2$) 0.41

IR (KBr) ν$_{max}$ 3356, 1608, 1509, 1464, 1251, 1178, 1033 cm$^{-1}$

U.V. (EtOH) λ$_{max}$ 227.5 (ε=47461), 204 (ε=79092) nm $^1$H (CDCl$_3$/d$_4$-MeOD) δ7.83 (s, H8), 7.62 (d, J=8 Hz, 2Ar H), 7.40 (d, J=8 Hz, 2ArH), 7.19 (d, J=8 Hz, 4ArH), 6.74 (d, J=8 Hz, 4ArH), 5.53–5.45 (m, H1'), 4.65–4.55 (m, 2H, C H,H3'), 4.35–4.15 (m, 3H, H4'5'5'), 3.74 (s, 6H, 2OMe), 1.19 (d, J=7 Hz, 6H, 2Me) ppm FDMS for C$_{35}$H$_{37}$N$_7$O$_6$F$_2$ requires M689; Found m/z 689 (10),389 (30), 302 (25).

N-Isopropyl-4-[4-methoxyphenyl-4'methylphenyl-6-N-[2-amino-9-(2'-deoxy-2',2'-difluoro-β-ribofuranosyl)purinyl]methyl]benzamide Active ester (50 mg) was reacted with isopropylamine, according to General Procedure F, to give the amide as a white soild (43.6 mg; 95%)

Tlc Rf (10% MeOH/CH$_2$Cl$_2$) 0.41

IR (KBr) $v_{max}$ 3360, 1607, 1510, 1465, 1252, 1076, 1036 cm$^{-1}$

U.V. (EtOH) $\lambda_{max}$ 205 ($\epsilon$=72094) nm $^1$H (d$_4$-MeOD) δ7.95 (s, H8), 7.67 (d, J=8 Hz, 2ArH), 7.45 (d, J=8 Hz, 2ArH), 7.22 (t, J=8 Hz, 4ArH), 7.07 (d, J=6 Hz, 2ArH), 6.79 (dd, J=2, 8 Hz, 2ArH), 5.60–5.47 (m, H1'), 4.40–4.27 (m, H3'), 4.23–4.10 (m, CH), 3.90–3.70 (m, 3H, H4'5'5'), 3.75 (s, OMe), 2.27 (s, Me), 1.21 (d,J=7 Hz, 6H, 2Me) ppm FDMS for C$_{35}$H$_{37}$N$_7$O$_5$F$_2$ requires M 673; Found m/z 673 (100), 372 (20), 302 (40).

N-Isopropyl-4-[4-methoxyphenyl-phenyl)-6-N-[2-amino-9-(2'-deoxy-2',2'-difluoro-β-ribofuranosyl)purinyl]methyl]benzamide Active ester (50 mg) was reacted with isopropylamine, according to General Procedure F, to give the amide as a white soild (36 mg; 78%)

Tlc Rf (20% MeOH/CH$_2$Cl$_2$) 0.68

IR (KBr) $v_{max}$ 3373, 1609, 1511, 1466, 1253, 1077 cm$^{-1}$

U.V. (EtOH) $\lambda_{max}$ 224 ($\epsilon$=42444), 204.5 ($\epsilon$=68723) nm $^1$H (d$_6$-acetone) δ7.80 (s, H8), 7.72 (d, J=6 Hz, 2ArH), 7.46 (d, J=6 Hz, 2ArH), 7.42–7.36 (m, 2ArH), 7.32–7.14 (m, 5ArH), 6.82 (d, J=8 Hz, 2ArH), 6.28 (s, NH), 6,10 (br s, N H$_2$), 5.80–5.65 (m, H1'), 5.42 (d, J=6 Hz, OH), 4.72–4.50 (m, 2H, OH, H3'), 4.28–4.10 (m, CH), 3.86–3.70 (m, 3H, H4'5'5'), 3.76 (s, OMe), 1.21 (d, J=6 Hz, 6H, 2Me) ppm FDMS for C$_{34}$H$_{35}$N$_7$O$_5$F$_2$ requires M659; Found m/z 659 (100), 358 (15);

N-Isopropyl-4-[4-methylphenyl-phenyl)-6-N-[2-amino-9-(2'-deoxy-2',2'-difluoro-β-ribofuranosyl)purinyl]methyl]benzamide Active ester (50 mg) was reacted with isopropylamine, according to General Procedure F, to give the amide as a white soild (36.1 mg; 78%)

Tlc Rf (10% MeOH/CH$_2$Cl$_2$) 0.51

IR (CHCl$_3$) $v_{max}$ 3358, 1633, 1427, 1077 cm$^{-1}$

U.V. (EtOH) $\lambda_{max}$ 204 ($\epsilon$=62080) nm $^1$H (d$_4$-MeOD) δ7.88 (s, H8), 7.67 (d, J=8 Hz, 2ArH), 7.46 (d, J=10 Hz, 2ArH), 7.34 (d, J=8 Hz, 2ArH), 7.26–7.12 (m, 5ArH), 7.05 (d, J=7 Hz, 2ArH), 5.60–5.46 (m, H1'), 4.41–4.24 (m, H3'), 4.23–4.10 (m, CH), 3.92–3.64 (m, 3H, H4'5'5'), 2.28 (s, Me), 1.22 (d, J=6 Hz, 2Me) ppm FDMS for C$_{34}$H$_{35}$N$_7$O$_4$F$_2$ requires M 644; Found m/z 644 (65)

N-Isopropyl-4-[bis-phenyl-6-N-[2-amino-9-(2'-deoxy-2',2'-difluoro-β-ribofuranosyl)purinyl]methyl] benzamide Active ester (50 mg) was reacted with isopropylamine, according to General Procedure F, to give the amide as a white soild (32 mg; 70%)

Tlc Rf (10% MeOH/CH$_2$Cl$_2$) 0.58 m.p. 190° C. (decomp.)

IR (KBr) $v_{max}$ 3362, 1633, 1467, 1077 cm$^{-1}$

U.V. (EtOH) $\lambda_{max}$ 205 ($\epsilon$=65359) nm $^1$H (d$_6$-acetone) δ7.80 (s, H8), 7.73 (d, J=8 Hz, 2ArH), 7.48 (d, J=8 Hz, 2ArH), 7.42–7.37 (m, 4ArH), 7.32–7.15 (m, ArH), 6.36 (s, NH), 6.12 (br s, NH$_2$), 5.78–5.64 (m, H1'), 5.43 (d, J=8 Hz, OH), 4.74–4.52 (m, 2H, OH, H3'), 4.26–4.16 (m, CH), 3.96–3.72 (m, 3H, H4'5'5'), 1.20 (d, J=6 Hz, 6H, 2Me) ppm FDMS for C$_{33}$H$_{33}$N$_7$O$_4$F$_2$ requires M 630; Found m/z 630 (70), 328 (20)

B. Schematic for Release Studies

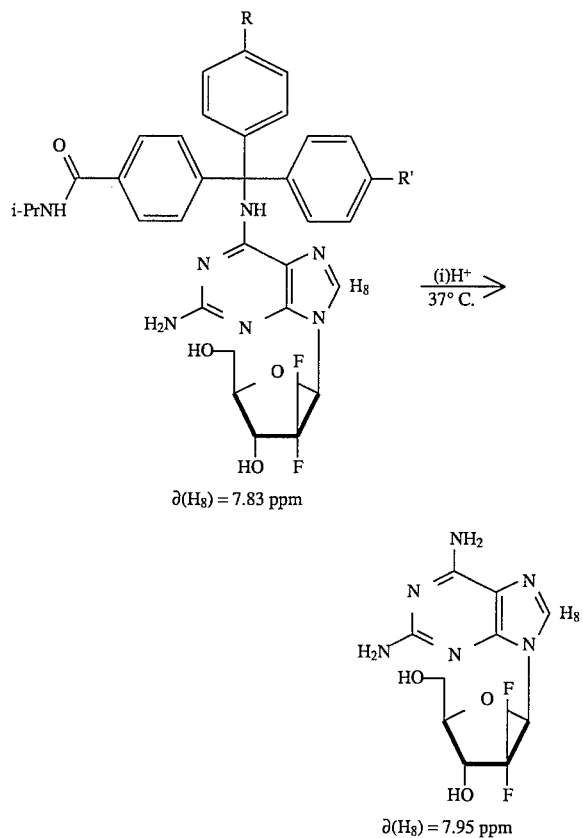

(i) ~6 mM in 0.1M KH$_2$PO$_4$ – D$_2$O buffer/d$_4$MeOH

C. Procedure for the release studies

The isopropylamide linker-drug (2 mg) was dissolved in 0.3 ml of dry deuterated methanol (CD$_3$OD). A solution of potassium phosphate buffer in deuteratured water (D$_2$O) (0.2 ml) of appropriate pH was added. The resulting solution was transferred to an NMR tube and heated at 37° C. and NMR spectra were recorded periodically. The rate of appearance of free drug and the rate of disappearance of the starting material were calculated from the peak integrals at:

| NMR spectra (CD$_3$OD/0.1M KD$_2$PO$_4$) | H$_8$ ∂/ppm |
|---|---|
| starting material | 7.83 |
| free drug | 7.95 |

TABLE V

| | $t_{1/2}$/h | | |
|---|---|---|---|
| R = | H | OMe | OMe |
| R' = | OMe | OMe | OMe |
| IPA | p | p | m |
| pH | | | |
| 5.40 | 16.7 | 3.71 | 2.35 |
| 6.40 | 547* | 14.8 | 23.3 |
| 7.40 | 800* | 146.3 | 133.3* |

*extrapolated
N.B. N6-trityl-ADDFA p-IPA showed no fragmentation under pH conditions used - up to t = 800

The compounds of Formula III have been shown to be active against human tumors in vitro. The in vitro data were obtained using CCRF-CEM cells, a human leukemia cell line. Foley et al., *Cancer*, 18:522 (1965). These cells were grown in albumin-free UltraCHO® media (BioWhittaker, Inc., Walkersville, Md.) using standard techniques. See, e.g., G. B. Grindey, et al., *Journal of Molecular Pharmacology*, 16:601 (1979). Dose-response curves were generated for various compounds to determine the concentration required for 50% inhibition of growth ($IC_{50}$). Cluster plates were prepared in duplicate with the compound at various concentrations. Test compounds were dissolved initially in DMSO at a concentration of 4 mg/ml and further diluted with solvent to the desired concentration. Cells in serum-free UltraCHO media were added to the well at a final concentration of $4.8 \times 10^4$ cells/well in a total volume of 2.0 ml. After 72 hours of incubation (95% air, 5% $CO_2$), cell numbers were determined on a ZBI Coulter counter. Cell number for indicated controls at the end of incubation was usually $(4-6) \times 10^5$ cells/well. Cell viability was also measured by staining with 3-[4,5-dimethylthiazol-2-yl]-2,5-diphenyl-tetrazolium bromide (MTT) using standard techniques. R. I. Freshhey, *Culture of Animal Cells: A Manual of Basic Technique*, 253–354 (2d ed. 1987).

Table VI, infra, shows the results of one such in vitro screening panel. Column 1 refers to the example number of the compound tested; Column 2 depicts the in vitro cytoxicity against CCRF-CEM cells by relating the concentration of the test compound required for 50% inhibition of growth ($IC_{50}$) of the cells in the well.

TABLE VI

In Vitro Antitumor Activity of N6-Trityl-ADDFA-iPA Prodrugs

| | R | R' | $IC_{50}$ (µg/ml) |
|---|---|---|---|
| ADDFA | | | 0.024 |
| mDMT | OMe | OMe | 0.084 |
| DMT | OMe | OMe | 0.078 |
| MMeT | OMe | Me | 0.1 |
| MMT | H | OMe | 0.1 |
| MeT | Me | H | 0.8 |
| T | H | H | 1.7 |

The compounds of Formula III has been shown to be active against transplanted mammalian tumors in vivo. To demonstrate the anti-tumor activity of the compounds of Formula III, the compound was tested in mice bearing xenograft tumors.

One of the tumor models used for showing the antineoplastic activity of the prodrugs of this invention were the human colon xenografts, HC-1 human colon xenograft. This tumor model was obtained from the Division of Cancer Treatment, National Cancer Institute, Tumor Bank.

First passage tumors were stored in liquid nitrogen, using standard techniques. The transplanted tumor was reestablished from the Tumor Bank every six months or as needed. The tumor was maintained by serial passage twice weekly in nude mice.

In the procedures utilized here, the tumor was removed from passage animals and minced into 1- to 3-mm cubic fragments using sterile techniques. Tumor pieces were checked for sterility using both Antibiotic Medium 1 and Brain Heart Infusion (Difco, Detroit, Mich.). The xenograft tumor pieces were implanted into the recipient CD1 Nu/Nu mice subcutaneously in an axillary site by trochar.

Drug therapy on the appropriate schedule was initiated 14 days after tumor implantation for the mice bearing the xenograft tumors. The compound being tested was mixed with 2.5% Emulphor EL620 from GAP Corporation (1:40 dilution in 0.9% saline). The total dosage volume for each administration was 0.5 ml. All animals were weighed at the beginning and end of administration of the subject compounds. Food and water were provided ad libitum.

Each control group and each dosage level of the treated groups consisted of 9 or 10 mice selected at random from the pool of implanted animals. The formulations were administered intraperitoneally. Compounds were dosed on days 1, 4, 7, and 10 for all prodrugs except for MMeT which was dosed on days 1,5, and 9.

The tumor was measured five days after treatment ended with two dimensional measurements (width and length) of the tumor taken using digital electronic calipers interfaced to a microcomputer. J. P. Worzalla, et al., *Investigational New Drugs*, 8:241–251 (1990). Tumor weights were calculated from these measurements using the following formula:

$$\text{Tumor weight (mg)} = \frac{\text{tumor length (mm)} \times [\text{tumor width (mm)}]^2}{2}$$

At least one control group of an equal number of mice was treated with the same volume of 2.5% Emulphor only. The percent inhibition is determined by subtracting the ratio of the mean tumor size of the test group relative to the control group from one and multiplying the result by 100.

The results of several experiments in mice bearing the HC-1 human colon carcinoma when the Formula III compounds were administered orally are provided in Table V. Row 1 describes the particular compound being tested. Row 15 describes the overall activity of the compound. Column 1 gives the dosage level of the compound of Formula III and ADDFA in mg/kg. The second column gives the percent inhibition of tumor growth by the ADDFA given systemically. Colums 3 through 7 gives the percent inhibition of tumor growth of the compounds of Formula III.

TABLE I

ANTITUMOR ACTIVITY OF TRITYLATED ADDFA PRODRUGS AGAINST HC-1 HUMAN COLON CARCINOMA XENOGRAFTS IN NUDE MICE

| Dosage (mg/kg) | Percent Inhibition | | | | | |
|---|---|---|---|---|---|---|
| | ADDFA | DMT | NMeT | MMT | MeT | T |
| 17.5 | 100 | | | | | 14 |
| 20.0 | 100 | | 95 | | 41 | |
| 25.0 | 100 | 97 | | | | |
| 32.5 | 100 | | | 95 | | |

TABLE I-continued

ANTITUMOR ACTIVITY OF TRITYLATED ADDFA PRODRUGS AGAINST HC-1 HUMAN COLON CARCINOMA XENOGRAFTS IN NUDE MICE

| Dosage (mg/kg) | Percent Inhibition | | | | | |
|---|---|---|---|---|---|---|
| | ADDFA | DMT | NMeT | MMT | MeT | T |
| 35.0 | 100 | | | | | 28 |
| 40.0 | 100 | | 98 | | 58 | |
| 50.0 | 100 | 99 | | | | |
| 65.0 | 100 | | | 96 | | |
| 70.0 | 100 | | | | | 04 |
| 80.0 | 100 | | 98 | | 92 | |
| 100.0 | 100 | 99 | | | | |
| 130.0 | 100 | | | 93 | | |
| Activity | +++ | +++ | +++ | +++ | ++ | − |

+++ 95–100% Inhibition
++ 80–94% Inhibition
+ 60–79% Inhibition
− <60% Inhibition Since the compounds of Formula I and Formula III are antineoplastic agents, the invention also provides a method of treating a susceptible neoplasm in a mammal which comprises administering to a mammal in need of said treatment an effective amount of a compound of Formula I, III, or a pharmaceutically acceptable salt or solvate thereof. In particular, the present compound is useful in treating solid tumors including carcinomas such as ovarian, non-small cell lung, gastric, pancreatic, prostate, renal cell, breast, colorectal, small cell lung, melanoma, and head and neck; and sarcomas such as Kaposi's sarcoma and rhabdomyosarcoma.

Immunoconjugate Formulations

The immunoconjugates of the present invention are useful in the treatment methods of the present invention, particularly when parenterally administered in pharmaceutical compositions which are also an aspect of the present invention.

Such compositions, comprising an immunoconjugate of Formula I and a parenterally-administrable medium, are formulated by methods commonly used in pharmaceutical chemistry. For example, the present immunoconjugates are acceptably soluble in physiologically acceptable fluids (carriers) such as physiological saline solutions, serum proteins such as human serum albumin, buffer substances such as phosphates, water, and electrolytes, and the like.

Products for parenteral administration are often formulated and distributed in a solid form preferably lyophilized, for reconstitution immediately before use. Such formulations are useful compositions of the present invention. Preparation of lyophilized compositions is well known in the art. Generally, such compositions comprise mixtures of inorganic salts which confer isotonicity, and dispensing agents, such as lactose, which allow the dried preparations to quickly dissolve upon reconstitution. Such formulations are reconstituted for use with highly purified water.

The most effective concentration of the immunoconjugates of the present invention in a composition of the present invention is dictated by the drug used in the conjugate, the physical properties of the drug and conjugate, and the final form of the composition. One skilled in the art of preparing such compositions will readily recognize the variables to be considered and the optimal ratio of composition components.

Similarly, the most effective dosage regimen for the immunoconjugate composition of the present invention depends upon the severity and course of the disease/infection, the patient's health and response to treatment, and the judgment of the treating physician. Accordingly, the dosages of the immunoconjugates and any accompanying compounds should be titrated to the individual treatment. Otherwise, guidance to the specific potencies of drugs and their appropriate dosage ranges is to be obtained from the standard medical literature.

The present invention also provides methods for treating susceptible mammalian cells or tissues comprising administering an effective amount of an immunoconjugate of Formula I above to a mammal in need of such treatment.

Furthermore, the present invention provides a method of inhibiting the growth of pathogens in a mammalian host comprising administering an effective amount of an immunoconjugate of Formula I above to a mammal in need of such treatment.

Alternative embodiments of the methods of this invention include the administration, either simultaneously or sequentially, of a number of different immunoconjugates bearing different drugs, or different antibodies or antigen-binding fragments thereof, for use in methods of combination chemotherapy.

The conjugates and compositions comprising the conjugates are used for treatment of patients who are in need of treatment with the drug comprised by the conjugate. The specific purpose of the treatment, and the dose range to be administered, depends on the identity of the drugs and the condition for which the patient is to be treated. Guidance as to the specific potencies of drug and their appropriate dosage ranges is to be obtained from the standard medical literature.

Prodrug Formulations

The compounds of Formula III are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The present invention also includes pharmaceutical compositions which contain, as the active ingredient, the compounds of Formula III associated with pharmaceutically acceptable carriers. In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Prodrug Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Prodrug Formulation Example 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Prodrug Formulation Example 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

Prodrug Formulation Example 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Prodrug Formulation Example 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Prodrug Formulation Example 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Prodrug Formulation Example 7

Suspensions, each containing 50 mg of medicament per 5.0 ml dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Prodrug Formulation Example 8

Capsules, each containing 15 mg of medicament, are made as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Prodrug Formulation Example 9

An intravenous formulation may be prepared as follows:

| Ingredient | Quantity |
| --- | --- |
| Active Ingredient | 250.0 mg |
| Isotonic saline | 1000 ml |

Prodrug Formulation Example 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Prodrug Formulation Example 11

Sublingual or buccal tablets, each containing 10 mg of active ingredient, may be prepared as follows:

| Ingredient | Quantity Per Tablet |
| --- | --- |
| Active Ingredient | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate,

What is claimed is:

1. A compound of the formula:

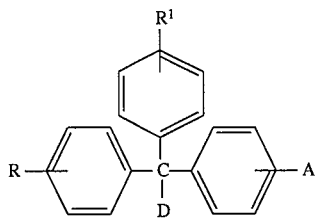

wherein:

R and R¹ are independently selected from the group consisting of:
—NO₂, —CHO, —COOH, —CO₂X, —PO₂X, —CBR₃, —CCl₃, —CF₃, —Cl₃, —COX, —CN, —CONH₂, —OC(O)OX, —OC(O)NHX, —OC(O)NX₂, —CH₂Cl, —CH₂X, —CH₃, —CHX₂, —CX₃, —F, —Cl, —Br, —I, —H, —NH₂, —SH, —OPOX, —OH, —OX, —OCO₂X, —SX, —SONH₂, —S(O)ₙX, —SO₂NH₂, —SO₂NHX, —SONHX, —NHX, and —NX₂,
where X is C₁–C₁₂ alkyl or aryl,
and n is 0–3;

D is a drug selected from the group consisting of doxorubicin, gemcitabine and 2-Amino-2'-deoxy-2',2'-difluoroadenosine;

A is

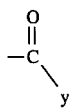

wherein:
y is C₁–C₁₂ alkyl, C₂–C₁₂ alkenyl, C₂–C₁₂ alkynyl, C₁–C₁₂ alkoxy, C₁–C₁₂ alkylthio, C₁–C₁₂ alkylamino, aryl, arylamino, aralkylamino, arylthio, aryloxy, aralkyl, aralkylamino, aralkalkyamino, aralkylthio, aralkoxy, or a peptide having from 2–6 amino acids,
or a salt or solvent thereof.

2. The compound of claim 1 wherein R and R' are independently selected from the group consisting of hydroxy, C₁–C₁₂ alkoxy, C₁–C₁₂ alkyl, C₁–C₁₂ alkanoyl, di(C₁–C₁₂ alkyl)amino, C₁–C₁₂ alkylamino, trichloromethyl, and trifluoromethyl, or a pharmaceutically acceptable salt or solvate thereof.

3. The compound of claim 2 wherein R and R' are independently selected from the group consisting of hydroxy, C₁–C₆ alkoxy, C₁–C₆ alkyl, di(C₁–C₆ alkyl)amino, and C₁–C₆ alkylamino, or a pharmaceutically acceptable salt or solvate thereof.

4. The compound of claim 3 wherein R and R' are independently selected from the group consisting of hydroxy and C₁–C₆ alkoxy, or a pharmaceutically acceptable salt or solvate thereof.

5. The compound of claim 1 wherein D is doxorubicin.

6. The compound of claim 1 wherein D is gemcitabine.

7. The compound of claim 1 wherein D is 2-Amino-2'-deoxy-2',2'-difluoroadenosine.

8. A compound of the formula:

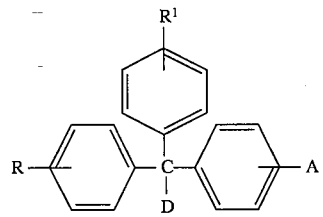

wherein:

R and R¹ are each —OCH₃;

A is

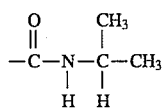

and D is

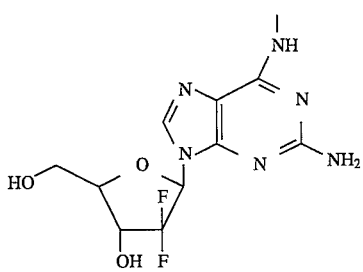

* * * * *